US012758568B2

(12) United States Patent
Nakazawa et al.

(10) Patent No.: US 12,758,568 B2
(45) Date of Patent: Oct. 13, 2026

(54) AGENT FOR ADJUSTING HARDNESS OF LENS OF EYE

(71) Applicant: NAGASE VIITA CO., LTD., Okayama (JP)

(72) Inventors: Yosuke Nakazawa, Tokyo (JP); Naoki Morishita, Okayama (JP); Shin Endo, Okayama (JP); Masaki Miyake, Okayama (JP); Hitoshi Mitsuzumi, Okayama (JP); Motoshi Hayano, Tokyo (JP); Kazuo Tsubota, Tokyo (JP)

(73) Assignee: NAGASE VIITA CO., LTD., Okayama (JP)

( * ) Notice: Subject to any disclaimer, the term of this patent is extended or adjusted under 35 U.S.C. 154(b) by 402 days.

(21) Appl. No.: 18/253,155

(22) PCT Filed: Nov. 15, 2021

(86) PCT No.: PCT/JP2021/041978
§ 371 (c)(1),
(2) Date: May 16, 2023

(87) PCT Pub. No.: WO2022/107735
PCT Pub. Date: May 27, 2022

(65) Prior Publication Data

US 2024/0148766 A1 May 9, 2024

(30) Foreign Application Priority Data

Nov. 17, 2020 (JP) ................................ 2020-191266
Jan. 14, 2021 (JP) ................................ 2021-004576

(51) Int. Cl.

| | |
|---|---|
| *A61K 31/7048* | (2006.01) |
| *A23C 9/13* | (2006.01) |
| *A23G 3/36* | (2006.01) |
| *A23G 4/12* | (2006.01) |
| *A23L 2/52* | (2006.01) |
| *A23L 27/30* | (2016.01) |
| *A23L 33/00* | (2016.01) |
| *A23L 33/125* | (2016.01) |
| *A23L 33/15* | (2016.01) |
| *A61K 9/00* | (2006.01) |
| *A61K 9/16* | (2006.01) |
| *A61K 9/20* | (2006.01) |
| *A61K 9/48* | (2006.01) |
| *A61K 9/68* | (2006.01) |
| *A61K 47/02* | (2006.01) |
| *A61K 47/12* | (2006.01) |
| *A61K 47/26* | (2006.01) |
| *A61K 47/46* | (2006.01) |
| *A61P 27/10* | (2006.01) |

(52) U.S. Cl.
CPC ........ *A61K 31/7048* (2013.01); *A23C 9/1307* (2013.01); *A23C 9/1322* (2013.01); *A23G 3/368* (2013.01); *A23G 4/126* (2013.01); *A23L 2/52* (2013.01); *A23L 27/30* (2016.08); *A23L 33/125* (2016.08); *A23L 33/15* (2016.08); *A23L 33/40* (2016.08); *A61K 9/0053* (2013.01); *A61K 9/0056* (2013.01); *A61K 9/0058* (2013.01); *A61K 9/0095* (2013.01); *A61K 9/1623* (2013.01); *A61K 9/2013* (2013.01); *A61K 9/2018* (2013.01); *A61K 9/2068* (2013.01); *A61K 9/4825* (2013.01); *A61K 9/4858* (2013.01); *A61K 9/4875* (2013.01); *A61K 47/02* (2013.01); *A61K 47/12* (2013.01); *A61K 47/26* (2013.01); *A61K 47/46* (2013.01); *A61P 27/10* (2018.01)

(58) Field of Classification Search
None
See application file for complete search history.

(56) References Cited

U.S. PATENT DOCUMENTS

| | | | | |
|---|---|---|---|---|
| 5,627,157 A * | 5/1997 | Hijiya | .................... | C12P 19/16 514/25 |
| 2009/0171327 A1 | 7/2009 | Kurtz et al. | | |
| 2013/0085482 A1 | 4/2013 | Van Valen et al. | | |
| 2017/0081354 A1* | 3/2017 | Kambe | .................. | C12P 19/14 |

(Continued)

FOREIGN PATENT DOCUMENTS

| | | | |
|---|---|---|---|
| JP | 2009007256 | A | 1/2009 |
| JP | 2015013175 | A | 1/2015 |
| JP | 2015-140327 | A | 8/2015 |
| JP | 2018187402 | A | 11/2018 |
| JP | 2019-156742 | A | 9/2019 |
| WO | 2016/031869 | A1 | 3/2016 |
| WO | 2016/068278 | A1 | 5/2016 |

OTHER PUBLICATIONS

Nakazawa, Y., Oka, M., Tamura, H., & Takehana, M. (2016). Effect of hesperetin on chaperone activity in selenite-induced cataract. Open Medicine, 11(1), 183-189. (Year: 2016).*

(Continued)

*Primary Examiner* — Dale R Miller
(74) *Attorney, Agent, or Firm* — FISHERBROYLES, LLP; Roger L. Browdy

(57) ABSTRACT

An object of the present invention is to provide a novel agent for adjusting hardness of a lens of an eye which can be taken easily, conveniently, and safely for a long-term, can effectively adjust the hardness of the lens, and is capable of preventing, alleviating and improving poor focus and decreased near visual acuity, such as presbyopia, caused by aging and various diseases. The present invention solves the above object by providing an agent for adjusting hardness of a lens of an eye comprising a glycosyl hesperetin as an active ingredient.

9 Claims, 7 Drawing Sheets

(56) References Cited

U.S. PATENT DOCUMENTS

| | | | | |
|---|---|---|---|---|
| 2017/0246122 | A1 | 8/2017 | Higuchi et al. | |
| 2017/0246176 | A1 | 8/2017 | Tsubota | |
| 2021/0030780 | A1* | 2/2021 | Van Aken .......... | A61K 31/7076 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002 (Year: 2002).*

Nakazawa Y. et al. Effect of alpha-glucosyl hesperidin consumption on Lens Sclerosis and Presbyopia, Cells, 2021, vol. 10, No. 2, p. 382.

Michael R. et al. The ageing lens and cataract: a model of normal and pathological ageing Philosophical Transactions, 2011, vol. 366, No. 1568 p. 1278-1292.

Nakazawa Y. et al. Oral consumption of alpha glucosyl hesperidin could prevent lens hardening, which causes presbyopia, Biochemistry and Biophysics Reports, 2021, vol. 25, p. 100885.

William H. Garner and Margaret H. Garner. Protein Disulfide Levels and Lens Elasticity Modulation: Applications for Presbyopia. Investigative Ophthalmology & Visual Science 2016, 57 (6), pp. 2851-2863.

Manikandan, Ramar, and Munuswamy Arumugam. "Anticataractogenic effect of hesperidin in galactose-induced cataractogenesis in Wistar rats." World Journal of Ophthalmology 6.1 (2016): pp. 1-9.

Nakazawa, Yosuke, et al. "Hesperetin prevents selenite-induced cataract in rats." Molecular vision 21 (2015): pp. 804-810.

"Ophthalmology Mini Guide—365 Days" Day 317Nuclear Cataract, published by Fudan University Press Co., Lid., Mar. 2014, p. 317.

International Search Report English Translation of PCT/JP2021/041978 dated Dec. 21, 2021.

Nakazawa, Yosuke et al. "Oral Intake of α-glucosyl-hesperidin Ameliorates Selenite-induced Cataract Formation", Molecular Medicine Reports. Jan. 14, 2020, vol. 21, No. 3, pp. 1258-1266.

Laser Cataract Surgery of Core Hardness 5 (Hardest Lens), Aoyama Eye Clinic <URL: https://www.aoyama-eye.com/news/2411/>, Jun. 16, 2017.

Cataracts. Keio Hospital Information & Patient Assistance Service (KOMPAS) <URL: https://kompas.hosp.keio.acjp/contents/000207.html>, Feb. 20, 2018.

Food with Function Claim "Healthy Body Hesperidin" To Be Released through Itoen Official Mail Order Store "Healthy Body" Beginning Monday, Oct. 29, Itoen Press Release <URL: https://www.itoen.co.jp/news/detail/id=25242>, Oct. 25, 2018.

* cited by examiner

AGENT FOR ADJUSTING HARDNESS OF LENS OF EYE

TECHNICAL FIELD

The present invention relates to an agent for adjusting hardness of a lens of an eye, comprising a glycosyl hesperetin as an active ingredient, and more specifically to an agent for softening a lens of an eye or an agent for inhibiting hardening of a lens of an eye.

BACKGROUND ART

Presbyopia is said to affect all humans over the age of 40, and it is estimated that 65 million people in Japan and 1.8 billion people in the world are affected by presbyopia. In today's aging society, presbyopia is regarded as an important problem that directly affects quality of life (QOL), and effective countermeasures against presbyopia are desired. In addition, in recent years, the incidence of not only typical presbyopia that occurs with aging but also early onset presbyopia is becoming known, i.e., it is becoming clear that even relatively young children may have difficulty in focusing and complain of symptoms of presbyopia. It is getting increasingly important to develop countermeasures against presbyopia that can be easily and safely applied to a wider range of generations.

Presbyopia is caused by a decline in the ability of the eye to adjust focusing, and refers to a condition in which it is difficult to see nearby objects. As it typically occurs with aging, it is also commonly called "aged eyes". The lens of the eye is the tissue that refracts light. When looking at distant objects, focus of the lens is adjusted by relaxing the muscles around the lens (the ciliary muscles) and thereby decreasing the thickness of the lens. Conversely, when looking at nearby objects, focus of the lens is adjusted by contracting the ciliary muscles and thereby increasing the thickness of the lens. However, due to causes such as aging, the aforementioned ciliary muscle's strength weakens or the lens itself hardens and loses its elasticity, making it difficult to adjust focus and decreasing the ability to see, especially, nearby objects (i.e., near visual acuity).

It is thought that by properly adjusting and maintaining the elasticity of the lens, it may be possible to prevent, alleviate and improve poor focus and decreased near visual acuity, such as presbyopia.

Visual acuity correction using presbyopia glasses, presbyopia contact lenses, and so on is generally considered an option as a countermeasure against presbyopia. However, living with presbyopia glasses or presbyopia contact lenses involves tediousness of putting them on and taking them off. If presbyopia can be prevented, alleviated and improved, for example, by taking daily supplements, QOL will be significantly improved.

Under such circumstances, in recent years, various techniques for adjusting hardness of the lens of the eye have been reported. For example, a hardening inhibitor and a therapeutic agent for the lens tissue, which utilize bioactive compounds such as various cytokines obtained by culturing mesenchymal stem cells, have been reported (Patent Literature 1). On the other hand, a lens hardening inhibitor and a therapeutic and/or prophylactic agent for diseases associated with the lens hardening, which contain pirenoxines or salts thereof and/or tiopronins or salts thereof, are reported (Patent Literature 2), a lens hardening inhibitor and a therapeutic and/or prophylactic agent for diseases associated with lens hardening, which contain selenium compound such as selenium-binding lactoferrin or a salt thereof as an active ingredient (Patent Literature 3), and a pharmaceutical composition for prevention and/or treatment of keratoconjunctival disease or presbyopia, which contains a stilbene compound as an active ingredient (Patent Literature 4), have been reported. However, these agents are pharmaceuticals and have the disadvantages that they cannot be taken easily, conveniently, and safely for a long period of time.

CITATION LIST

Patent Literature

[Patent Literature 1] Japanese Patent Application Publication No. 2019-156742

[Patent Literature 2] International Publication No. WO2016-068278

[Patent Literature 3] Japanese Patent Application Publication No. 2015-140327

[Patent Literature 4] International Publication No. WO2016-031869

SUMMARY OF INVENTION

Technical Problem

The present invention has been made in view of the above-mentioned prior art, and an object of the present invention is to provide a novel agent for adjusting hardness of a lens of an eye, which can be taken easily, conveniently, and safely for a long period of time, can effectively adjust hardness of the lens, and is capable of preventing, alleviating and improving poor focus and decreased near visual acuity such as presbyopia.

Solution to Problem

The inventors of the present invention have accumulated intensive research efforts in order to solve the above object and unexpectedly found that oral ingestion of a glycosyl hesperetin can adjust hardness of the lens of the eye, in more detail, can inhibit hardening of the lens, and moreover can soften the lens once hardened, and thereby accomplished the agent for adjusting hardness of a lens of an eye of the present invention.

In other words, the present invention, in one embodiment, solves the above object by providing an agent for adjusting hardness of a lens of an eye, comprising a glycosyl hesperetin as an active ingredient.

Effects of Invention

An agent for adjusting hardness of a lens of an eye according to one embodiment of the present invention is the agent comprising a glycosyl hesperetin as an active ingredient, which can be taken by humans daily, continuously, safely, easily, and orally without discomfort, and in addition can be provided industrially at low cost. In one embodiment, an agent for adjusting hardness of a lens of an eye according to the present invention can effectively inhibit hardening of the lens, and can soften the lens once hardened.

DESCRIPTION OF EMBODIMENTS

Figure 1:
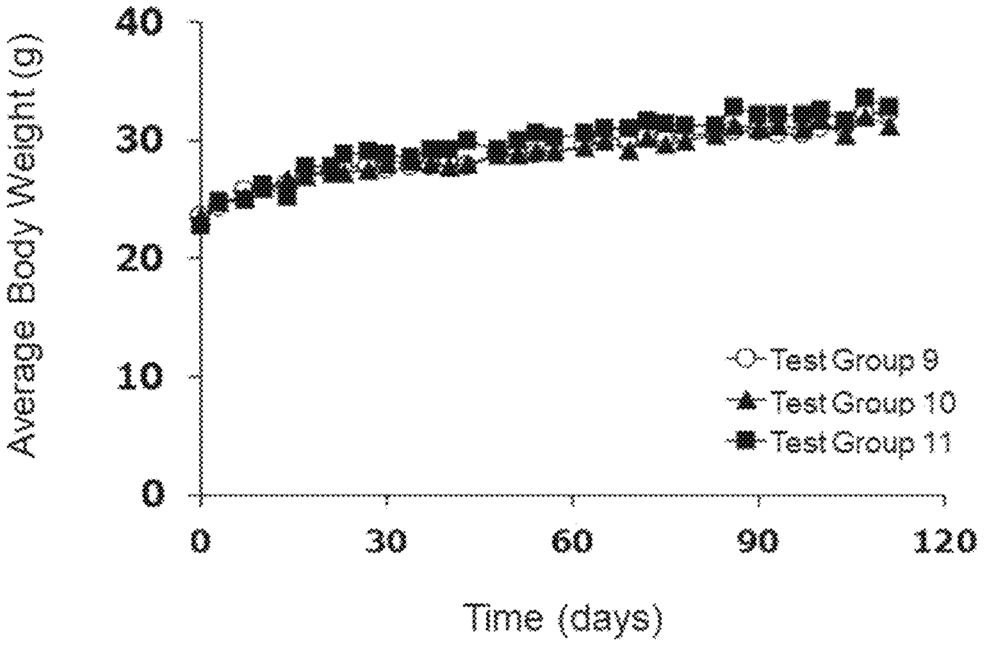
FIG. 1 The figure showing the change over time in body weight of test mice fed with a test sample containing glycosyl hesperetin or a control sample for 16 weeks.

The embodiment of the present invention will be described below, but they are only examples of preferred embodiment for carrying out the present invention, and the present invention is not limited to those embodiments.

In one aspect, the present invention relates to an agent for adjusting hardness of a lens of an eye, comprising a glycosyl hesperetin as an active ingredient, and a method for adjusting hardness of a lens of an eye, which uses a glycosyl hesperetin as an active ingredient.

The hardness of a lens of an eye referred to in the present specification means the degree of hardness of a lens of an eye, and more specifically, it refers to the hardness of a lens of an eye evaluated by the magnitude of the load required to produce a certain amount of dent of the lens, as described later in the experiments. Therefore, hardening of the lens means increase of the hardness of the lens, and, in other words, it means increase of the load required to produce a certain amount of dent of the lens.

Adjusting hardness of a lens of an eye referred to in the present specification means inhibiting hardening of the lens or softening the lens that is once hardened.

Inhibiting hardening of a lens of an eye referred to in the present specification means maintaining hardness of the lens by preventing progress of hardening of the lens caused by various factors such as aging and disease. An agent for inhibiting hardening of a lens of an eye means an agent to prevent hardening of the lens or slow the progress of hardening of the lens. Softening of a lens of an eye referred to in the present specification means decreasing hardness of the lens. An agent for softening a lens of an eye means an agent to improve hardening of the lens, decrease hardness of the lens, or treat symptoms associated with hardening of the lens.

Glycosyl hesperetin used as an active ingredient of the agent for adjusting hardness of a lens of an eye of the present invention means compounds composed of hesperetin bonded with saccharide(s) in general. In one embodiment, the preferred examples of the glycosyl hesperetin include one or more compounds selected from hesperidin, α-glycosyl hesperidin, and 7-O-β-glycosyl hesperetin.

Hesperidin, also known as vitamin P, is a compound having a chemical structure represented by the below Chemical Formula 1, wherein a rutinose composed of a rhamnose and a glucose is bound to a hesperetin. It is contained abundantly in, for example, a peel of citrus fruits.

Chemical Formula 1

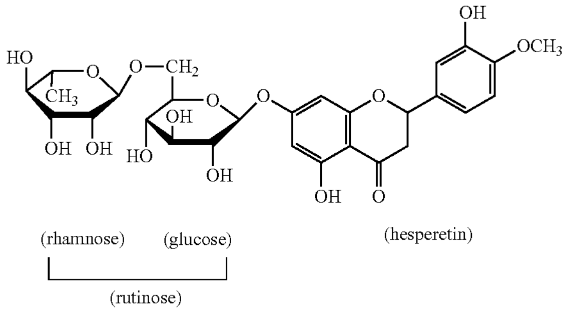

(rhamnose) (glucose) (hesperetin)

(rutinose)

Hesperidin (Chemical Formula 1)

On the other hand, 7-O-β-glucosyl hesperetin is a compound having a chemical structure represented by the below Chemical Formula 2, wherein a rhamnose residue of a rutinose residue comprised in hesperidin is removed, and has a higher water solubility than hesperidin. 7-O-β-glucosyl hesperetin may be prepared, for example, by allowing α-L-rhamnosidase (EC 3. 2. 1. 40) to act on a solution containing hesperidin, as described in Japanese Patent Application Publication No. H10-323196.

Chemical Formula 2

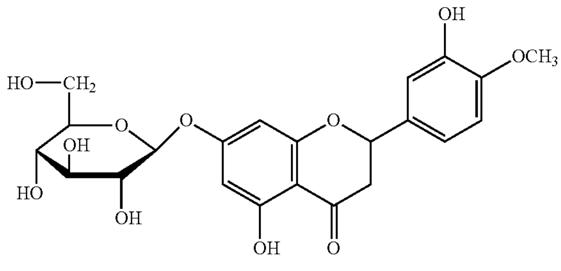

(glucose) (hesperetin)

7-O-β-Glucosyl Hesperetin (Chemical Formula 2)

Meanwhile, α-glycosyl hesperidins are compounds in which an equimolar or more saccharides (for example, saccharides such as D-glucose, D-fructose, or D-galactose) are bound to hesperidin via α-glycosidic bond. A representative example of α-glycosyl hesperidins includes α-glucosyl hesperidin (also known as an enzyme-treated hesperidin, saccharide-transferred or glycosyl hesperidin, water-soluble hesperidin, or saccharide-transferred or glycosyl vitamin P), which has a chemical structure represented by the below Chemical Formula 3, wherein one glucose molecule is bound to the glucose residue in the rutinose residue of hesperidin via α-1,4 glycosidic bond. As a product containing α-glucosyl hesperidin, for example, a product named "Hayashibara Hesperidin S" (commercialized by Hayashibara Co., Ltd., Okayama Japan) is commercialized.

Chemical Formula 3

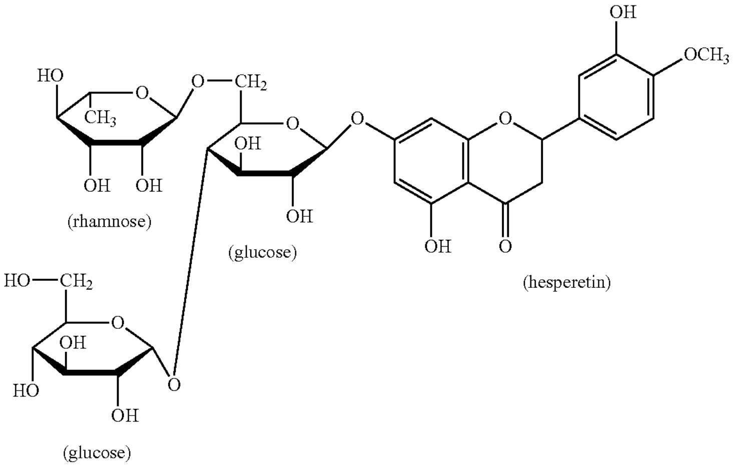

α-Glucosyl Hesperidin (Chemical Formula 3)

Glycosyl hesperetin is a safe and highly versatile substance that has been widely used as a material for various foods and beverages, cosmetics, quasi-drugs, pharmaceuticals, and so on. Among them, α-glycosyl hesperidin is more water soluble and is easier to handle compared to hesperidin and 7-O-β-glucosyl hesperetin. In the living body, α-glycosyl hesperidin is hydrolyzed to hesperetin by the action of enzymes similarly as hesperidin and 7-O-β-glucosyl hesperetin is, and exerts the original physiological activity of hesperetin.

In the present invention, any glycosyl hesperetin regardless of its origin, production method, purity and so on may be used as long as it is glycosyl hesperidin. In a preferred embodiment, a high-purity product containing less impurities may be suitably used. As the high-purity product, a highly purified glycosyl hesperetin obtained through a crystallization process or a highly purified glycosyl hesperetin obtained through a purification process using column chromatography may be included.

Hesperidin can be produced industrially in the desired amount, for example, by using fruits, peels of fruits, seeds, unripe fruits, etc. of citrus fruits, which are plants containing hesperidin, as raw materials and extracting from them using solvents such as water, alcohol, and so on appropriately. Meanwhile, α-glycosyl hesperidin can be produced industrially at low cost in the desired amount, for example, by allowing a glycosyltransferase to act on a solution containing hesperidin and α-glucosyl saccharide compounds to produce α-glycosyl hesperidin and collecting the thus produced α-glycosyl hesperidin, as disclosed in Japanese Patent Application Publication No. H11-346792. 7-O-β-Glucosyl hesperetin can be produced industrially at low cost in the desired amount by allowing α-L-rhamnosidase to act on hesperidin to produce 7-O-β-glucosyl hesperetin by making rhamnose being liberated from hesperidin and collecting the thus produced 7-O-β-glucosyl hesperetin.

In addition, the applicant of the present application improved the production method of glycosyl hesperetin with the aim of eliminating the miscellaneous taste, coloration, etc., which are considered to be the drawbacks of conventional glycosyl hesperetin, and has established a glycosyl hesperetin with the reduced miscellaneous taste, coloration and odor (hereinafter, "miscellaneous taste, coloration, and odor" may be collectively referred to as "miscellaneous taste and so on.") and a method for producing the same, which has been disclosed in International Publication No. WO2015/133483. The glycosyl hesperetin with reduced miscellaneous tastes and so on has the excellent advantage that it can be taken by humans daily, continuously, safely, easily and orally without discomfort, and that it can be provided industrially at low cost. Therefore, in one preferred embodiment of the present invention, the glycosyl hesperetin with reduced miscellaneous tastes and so on may be advantageously used as a preferred glycosyl hesperetin.

When simply referring to glycosyl hesperetin in the present specification, it may mean a glycosyl hesperetin mixture comprising one or more of hesperidin, α-glycosyl hesperidin, and 7-O-β-glucosyl hesperetin, unless otherwise specified. In one preferred embodiment of the present invention, a glycosyl hesperetin used as an active ingredient may be the one containing a α-glycosyl hesperidin, and more preferably the one containing a α-glucosyl hesperidin as a α-glycosyl hesperidin because the desired effect in the present invention, that is, the effect of inhibiting hardening of the lens, softening the lens, and so on, can be more remarkably exhibited.

As described above, in one embodiment, the glycosyl hesperetin comprised as an active ingredient in the agent for adjusting hardness of a lens of an eye of the present invention may be a composition comprising (1) one or more of hesperidin, α-glycosyl hesperidin (α-glucosyl hesperidin, and so on), and 7-O-β-glucosyl hesperetin, which are the compounds having a hesperetin skeleton, as a main ingredient, i.e., a glycosyl hesperetin mixture. The glycosyl hesperetin mixture may further comprise (2) flavonoids such as narirutin, diosmin, neoponcirin and glucosyl narirutin, and (3) trace components such as salts, which are considered to be derived from raw materials of the production or generated as by-products in the production process. In one embodiment, the glycosyl hesperetin comprised as an active ingredient in the agent for adjusting hardness of a lens of an eye of the present invention may comprise hesperetin to the extent that the desired effect of the present invention is not interfered. Herein, hesperetin may be the one whose dispersibility in solvents such as water has been enhanced by known physical or chemical methods, and so on.

In one embodiment, the glycosyl hesperetin or glycosyl hesperetin mixture, which are comprised as an active ingredient in the agent for adjusting hardness of a lens of an eye of the present invention, may be the glycosyl hesperetin content, on a dry solid basis, of 50% by mass or more but less than 100% by mass, preferably 60% by mass or more but less than 100% by mass, more preferably 70% by mass or more but less than 100% by mass, further preferably 80% by mass or more but less than 100% by mass, and more further preferably 85% by mass or more but less than 100% by mass. In one embodiment, the upper limit of the glycosyl hesperetin content on a dry solid basis of the glycosyl hesperetin or glycosyl hesperetin mixture, which are comprised as an active ingredient in the agent for adjusting hardness of a lens of an eye of the present invention, may be 99% by mass or lower, which can be provided in a relatively large amount industrially, easily, and at low cost, 98% by mass or lower in order to be provided at lower cost, and 97% by mass or lower in order to be provided at much lower cost. However, in the case that the glycosyl hesperetin content on a dry solid basis of the glycosyl hesperetin or glycosyl hesperetin mixture, which are comprised as an active ingredient in the agent for adjusting hardness of a lens of an eye of the present invention, is low, it may be inevitable to use a larger amount compared to when using those with the higher glycosyl hesperetin content and as a result, operation may become more complicated and handling may become poorer. Accordingly, in one preferred embodiment, the lower limit of the glycosyl hesperetin content may be 50% by mass or more, preferably 60% by mass or more, more preferably 70% by mass or more, further preferably 80% by mass or more, and further preferably 85% by mass or more.

The glycosyl hesperetin content referred to in the present specification means the sum of the content of all components that fall within the scope of a glycosyl hesperetin, on a dry solid basis, which may be determined by the following procedure using a composition containing glycosyl hesperetin as a sample: diluting or dissolving the sample with refined water to give a solution with a solid content concentration of 0.1 w/v %; filtering the resulting solution through a membrane filter with a pore size of 0.45 μm; subjecting the filtrate to high-performance liquid chromatography (HPLC) under the below described conditions with using a reagent grade hesperidin (FUJIFILM Wako Pure Chemical Corporation, Osaka, Japan) as a standard substance; calculating the content of each component that fall within the scope of a glycosyl hesperetin in the sample, on a dry solid basis, based on the area of a peak appeared in the chromatogram at the detection wavelength of 280 nm and the molecular weight of a compound, such as hesperidin, α-glycosyl hesperidin (α-glucosyl hesperidin, etc.), corresponding to the peak. A method for quantifying the content of each component that falls within the scope of a glycosyl hesperetin by the above explained HPLC analysis may be, for example, as described in below (1) to (4).

<Condition for HPLC Analysis>

HPLC Apparatus: "LC-20AD" (Shimadzu Corporation, Kyoto, Japan)

Degasser: "DGU-20A3" (Shimadzu Corporation, Kyoto, Japan)

Column: "CAPCELL PAK C18 UG 120" (Shiseido Company., Limited, Tokyo, Japan)

Detection: UV/VIS detector "SPD-20A" (Shimadzu Corporation, Kyoto, Japan)

Data processor: "CHROMATOPAC C-R7A" (Shimadzu Corporation, Kyoto, Japan)

Sample injection volume: 10 μL

Eluent: water/acetonitrile/acetic acid (80/20/0.01 (by volume ratio))

Flow rate: 0.7 ml/min

Temperature: 40° C.

Measurement wavelength: 280 nm

<Quantification of Glycosyl Hesperetin>

(1) Content of hesperidin: It is analyzed by HPLC, and calculated based on the ratio of a peak area of hesperidin in a sample to a peak area of a reagent grade hesperidin (FUJIFILM Wako Pure Chemical Corporation, Osaka, Japan) used as a standard substance at a predetermined concentration.

(2) Content of α-glucosyl hesperidin: It is analyzed by HPLC, and calculated based on the ratio of a peak area of α-glucosyl hesperidin in a sample to a peak area of a reagent grade hesperidin (FUJIFILM Wako Pure Chemical Corporation, Osaka, Japan) used as a standard substance at a predetermined concentration, and on the ratio of the molecular weight of α-glucosyl hesperetin to that of hesperidin.

(3) Content of 7-O-β-glucosyl hesperetin: It is analyzed by HPLC, and calculated based on the ratio of a peak area of 7-O-β-glucosyl hesperetin in a sample to a peak area of a reagent grade hesperidin (FUJIFILM Wako Pure Chemical Corporation, Osaka, Japan) used as a standard substance at a predetermined concentration, and on the ratio of the molecular weight of 7-O-β-glucosyl hesperetin to that of hesperidin.

(4) Contents of other glycosyl hesperetins: They are analyzed by HPLC, and calculated based on the ratio of a peak area of the other glycosyl hesperetins in a sample to a peak area of a reagent grade hesperidin (FUJIFILM Wako Pure Chemical Corporation, Osaka, Japan) used as a standard substance at a predetermined concentration, and on the ratio of the molecular weight of the other glycosyl hesperetins to that of hesperidin.

In one preferred embodiment, the glycosyl hesperetin comprised as an active ingredient in the agent for adjusting hardness of a lens of an eye of the present invention may be a α-glycosyl hesperidin comprising a α-glucosyl hesperidin. In this case, the preferred α-glucosyl hesperidin content of the glycosyl hesperetin may be usually, on a dry solid basis, 60% by mass or more but less than 100%, preferably 70% by mass or more but less than 100% by mass, more preferably 75% by mass or more but less than 100% by mass. The upper limit of the α-glucosyl hesperidin content of the glycosyl hesperetin comprised as an active ingredient in the agent for adjusting hardness of a lens of an eye of the present invention may be basically less than 100% by mass, as described above. However, in one preferred embodiment, from the viewpoint of providing the agent for adjusting hardness of a lens of an eye of the present invention at lower cost, the upper limit of the α-glucosyl hesperidin content of the glycosyl hesperetin comprised as an active ingredient in the agent of the present invention, may be usually 99% by mass or lower, preferably 95% by mass or lower, and more preferably 90% by mass or lower, which can be provided in a relatively large amount industrially, easily, and at low cost. Meanwhile, in one preferred embodiment, the α-glucosyl hesperidin content of the glycosyl hesperetin comprised as an active ingredient of the agent for adjusting hardness of a lens of an eye of the present invention, may be usually 60% by mass or more, preferably 70% by mass or more, and more preferably 75% by mass or more, for the same reasons as described for the glycosyl hesperetin content of the glycosyl hesperetin mixture.

Meanwhile, the amount of intake of the agent for adjusting hardness of a lens of an eye of the present invention may be any amount and it can be appropriately adjusted depending on, for example, the frequency of the intake and the condition of a person who takes the agent, etc. In a preferred embodiment, when all glycosyl hesperetins comprised in the agent for adjusting hardness of a lens of an eye of the present invention is considered as hesperidin and converted to mass (hereinafter, simply referred to as "hesperidin equivalent" in the present specification), the amount of intake of the agent of the present invention in hesperidin equivalent may be usually in the range of 0.2 to 100 mg/kg, preferably in the range of 0.4 to 80 mg/kg, more preferably in the range of 0.6 to 40 mg/kg, further preferably in the range of 0.8 to 20 mg/kg, and further preferably in the range of 1.0 to 10 mg/kg, per day. In other words, for example, when the agent for adjusting hardness of a lens of an eye of the present invention is taken by a person with a body weight of 50 kg, the amount of intake in hesperidin equivalent may be usually in the range of 10 to 5,000 mg, preferably in the range of 20 to 4,000 mg, more preferably in the range of 30 to 2,000 mg, further preferably in the range of 40 to 1,000 mg, and further preferably in the range of 50 to 500 mg, per day. The number of intakes may be any times. The agent for adjusting hardness of a lens of an eye of the present invention may be taken for any period. For example, it may be taken for one time to several times. In a preferred embodiment, it may be taken for a period of usually one week or longer, preferably two weeks or longer, more preferably four weeks or longer, further preferably eight weeks or longer, and further preferably twelve weeks or longer. When the amount of intake is below the lower limit, the desired effect may be significantly reduced or may not be exerted. When the amount of intake is above the upper limit, the effect may not be commensurate with the dosage, which may not desirable from the viewpoint of economic efficiency.

As discussed above, the agent for adjusting hardness of a lens of an eye according to one embodiment of the present invention may comprise various glycosyl hesperetins as active ingredients. Although the details are described later, the effect of inhibiting hardening of the lens and/or the effect of softening the lens may be effectively exerted in humans, for example, by continuous and daily oral ingestion of the agent for adjusting hardness of a lens of an eye of the present invention comprising a glycosyl hesperetin as an active ingredient. In a preferred embodiment, the agent for adjusting hardness of a lens of an eye of the present invention comprising a glycosyl hesperetin as an active ingredient may be used not only as a so-called functional food for preventing, alleviating, or improving poor focus or decline of near visual acuity, such as presbyopia, caused by aging and various diseases, but also be used as a functional food for preventing, alleviating, and improving various symptoms, diseases, increased fall risk, etc. which are caused by poor focus or decline of near visual acuity, such as presbyopia. Such symptoms include eye fatigue, blurred vision, eye pain, dry eye, stiff neck, headache, neck/shoulder/arm/back pain or dullness, numbness in limbs, dizziness, insomnia, increased stress, decreased activity, weight loss, decreased muscle strength, decreased muscle mass, decreased bone strength, decreased bone density, decreased vitality, decreased cognitive function, and depression. Meanwhile, such diseases include eye diseases with aging including cataract, glaucoma, retinal detachment, retinopathy, maculopathy, choroidal neovascularization, posterior staphyloma, optic neuropathy, etc. The agent for adjusting hardness of a lens of an eye of the present invention comprising a glycosyl hesperetin as an active ingredient may be used also as supplements, health foods, health supplements, beauty foods, dietary supplements, foods with nutrient function claims, foods with health claims, foods with functional claims, foods for specified health uses, foods for special dietary uses, quasi-drugs, and pharmaceuticals. In a preferred embodiment, the agent for adjusting hardness of a lens of an eye of the present invention comprising a glycosyl hesperetin as an active ingredient may be appropriately formulated into other functional foods, health foods, beauty foods, food with nutrient function claims, foods with health claims, foods with functional claims, foods for specified health use, quasi-drugs, pharmaceuticals, or foods and beverages.

As shown in the later described experiments, in a preferred embodiment, the agent for adjusting hardness of a lens of an eye of the present invention may be used for preventing, alleviating, and improving decline of near visual acuity, in particular, for preventing, alleviating, and improving decline of near visual acuity with aging. Herein, the near visual acuity is the visual acuity at a distance of about 30 to 40 cm, and preferably may be the one measured under refractive correction with binocular distance vision of 0.7 or more in decimal visual acuity. Preventing, alleviating, and improving near visual acuity may include delaying decline of near visual acuity, reducing the degree of near visual acuity loss, and increasing near visual acuity. When the agent for adjusting hardness of a lens of an eye of the present invention is used for preventing, alleviating, and improving decline of near visual acuity, the subject of administration may be any subject. In a preferred embodiment, the subject of administration may be a subject with an average near point distance of 15 to 45 cm, preferably a subject with an average near point distance of 20 to 40 cm, more preferably a subject with an average near point distance of 25 to 35 cm, under refractive correction with binocular distance vision of 0.7 or more in decimal visual acuity. Herein, the near point distance is the closest distance at which an object can be seen in focus. The near point distance may be measured, for example, by the method shown in the later described experiments. On the other hand, the subject of administration may be of any age. In a preferred embodiment, the subject of administration may be an adult, and more preferably the age of the subject may be in the range of 20 to 70 years old, further preferably in the range of 30 to 60 years old, further preferably in the range of 40 to 50 years old, and further more preferably in the range of 45 to 50 years old, from the viewpoint that decrease in near visual acuity with aging is significantly observed in these ages. However, it goes without saying that a subject of administration may be under the age of 20. In recent years, it is becoming known that the symptoms of poor focus and presbyopia can be seen also in relatively young children. In one embodiment, the agent for adjusting hardness of a lens of an eye of the present invention may be preferably used for preventing, alleviating, or improving the symptoms of poor focus and presbyopia in such relatively young children, for example, those under the age of 20.

In a preferred embodiment, the agent for adjusting hardness of a lens of an eye comprising a glycosyl hesperetin may be used in combination with one or more ingredients such as other plant- and animal-derived substances, their extracts or compounds that have the effects of preventing or alleviating decline of visual acuity and improving visual acuity, since the effect of inhibiting hardening of the lens and the effect of softening the lens exerted by glycosyl hesperetin may be more effectively exerted, and also since prevention, alleviation, and improvement effect of the aforementioned symptoms, such as decline of near visual acuity or poor focus due to presbyopia, as well as the aforementioned various diseases may be more effectively shown.

Other animal- and plant-derived substances, their extracts, or compounds that have the effect of preventing or alleviating decline of visual acuity and improving visual acuity include, animal-derived substance such as bovine gallstones, Shinju (pearl), Borei (ostreae testa), Mamushi (*agkistrodon halys*), earthworm epidermis, Yutan (bear bile), Reiyoukaku (antelope horn), Rokujo (antler velvet) and their extracts; plants such as Artichoke (*Cynara scolymus*), Eyebright (*Euphrasia officinalis*), Japanese ash (*Fraxinus lanuginosa*), Canadian clearweed (*Pilea mongolica*), lam bsquarters (*Chenopodium album* L.), Asian madder (*Rubia argyi*), Akayaziou (*Glutinous rehmannia*), Japanese silverberry (*Elaeagnus umbellata*), Agrimony, Agni fruit, five-leaf akebia (*Akebia quinata*), Acai fruit (fruit of *Euterpe oleracea*), Asatsuki (*Allium schoenoprasum* var. *foliosum*), Asafoetida, Ashwagandha (*Withania somnifera*), Asunaro (*Thujopsis dolabrata*), Acacia *catechu* (*Senegalia catechu*), Aji Amarillo (*Capsicum baccatum*), Aji Limon (*Capsicum baccatum*), Turnip (*B. rapa* var. *nippo-oleifera*), Chinese cork oak (*Quercus variabilis*), Jiaogulan (*Gynostemma pentaphyllum*), Anise (*Pimpinella anisum*), American witch-hazel (*Hamamelis virginiana*), Alistin, wolf's bane (*Arnica montana*), *Angelica*, Barrenwort (*Epimedium grandiflorum*), Japanese knotweed (*Fallopia japonica* (Houtt.) Ronse Decr var. *japonica*), Italian parsley, *Ginkgo biloba, Pyrola japonica, Fragaria, Lilium pumilum* (*Lilium tenuifolium*), *Gloiosiphonia capillaris*, Catnip (*Nepeta cataria*), *Ficus erecta*, Dill (*Anethum graveolens*), Bark of *Tabebuia* spp., *Acer palmatum, Lilium maculatum*, Neem Tree (Azadirachta indica), Fennel (*Foeniculum vulgare*), Witch-hazel (*Hamamelis virginiana*), Wintergreen (*Gaultheria procumbens*), Turmeric (*Curcuma longa*), Marsh mallow (*Althaea officinalis*), Japanese spikenard (*Aralia cordata*), Ume (*Prunus mume*), Japanese willowleaf oak (*Quercus salicina*), Ulupica (*Capsicum cardenasii*), *Epimedium brevicomum, Rosa multiflora*, purple coneflower (*Echinacea purpurea*), Egoma (*Perilla frutescens*), Shallot (*Allium ascalonicum*), Siberian Ginseng (*Eleutherococcus senticosus*), Scotch Broom (*Cytisus scoparius*), *Gentianella alborosea* (Gilg) Fabris, Elder (*Sambucus nigra*), Yerba mate (*Ilex paraguariensis*), Oats (*Avena Sativa*), Allspice (Pimenta *dioica*), *Astragalus* Root (*Astragali radix*), Palmyra palm (*Borassus flabellifer*), *Phellodendron amurense*, Japanese goldthread (*Coptis japonica*), *Silybum marianum*, Orient vine (*Sinomenium acutum*), *Murraya koenigii, Plantago asiatica, Cardamine scutata*, Barley (*Hordeum vulgare*), *Salsola komarovii*, Asian Ginseng (*Panax ginseng*), *Lilium rubellum, Lapsana apogonoides, Lilium* lancifolium, Oregano (*Origanum vulgare*), Orange (*Citrus sinensis*), Kava (*Piper methysticum*), *Glechoma hederacea* subsp. *Grandis, Uncaria rhynchophylla*, Sichuan pepper (*Zanthoxylum bungeanum*), Pumpkin seed (Seed of *Cucurbita*), Bark of *Erythroxylum catuaba, Valeriana fauriei* Brig., *Lilium speciosum*, Turnip (*Brassica rapa* var. *rapa*), Kabosu (*Citrus sphaerocarpa*), Chamomile, Mustard (*Brassica juncea*), Trifoliate orange (*Citrus trifoliata*), Guarana (*Pauffinia cupana*), Roselle (*Hibiscus sabdariffa*), Cardamom, Curry tree (*Murraya koenigii*), *Asarum nipponicum*, Liquorice, Coltsfoot (*Tussilago farfara*), Balloon flower (*Platycodon grandiflorus*), *Rumex japonicus*, Tabasco pepper (*Capsicum frutescens*), Caraway, Victory onion (*Allium victorialis*), Apricot kernel, Kumquat, *Calendula officinalis, Betel* (*Piper betle*), *Clerodendron trichotomum, Mallotus philippinensis, Pueraria montana* var. *lobata*, Cape jasmine (*Gardenia jasminoides*), Cumin, Root of shrubby sophora (*Sophora flavescens*), Clary sage (*Salvia sclarea*), Wheel lily (*Lilium medeoloides A. Gray*), Walnut (*Juglans*), Grapefruit, Watercress (*Nasturtium officinale*), Clove, Black mustard (*Brassica nigra*), *Schizonepeta tenuifolia*, Caper (*Capparis spinosa*), *Cassia* seed (*Cassiae semen*), *Geranium thunbergii*, Lingonberry (*Vaccinium vitis-idaea* L.), Pepper (*Piper nigrum*), *Monochoria vaginails* var. *plantaginea*, Coriander (*Coriandrum sativum*), *Eisenia arborea* Areschoug, Pomegranate (*Punica granatum*), Sweet potatos (*Ipomoea batatas*), Jujube (*Zizyphus jujuba* Mill. var. *spinosa*), Saffron (*Crocus sativus*), Sarsaparilla (*Smilax regelii*), *Crataegus cuneata*, Japanese pepper (*Zanthoxylum piperitum*), *Citrus depressa, Angelica pubescens*, Shishito pepper (*Capsicum annuum*), *Perilla frutescens* var. *crispa*, Winged bean (*Psophocarpus tetragonolobus*), Root of purple gromwell (*Lithospermum erythrorhizon*), Bark/Tree branch/Root bark of Chinese cinnamon (*Cinnamomum cassia*), *Filipendula multijuga*, Chinese peony (*Paeonia lactiflora*), Jasmine (*Jasminum officinale*), Chinese peony (*Paeonia lactiflora*), lilyturf (*Ophiopogon japonicus*), Ginger (*Zingiber officinale*), *Cimicifuga* rhizome (*Cimicifugae rhizoma*), *Rheum palmatum, Aster scaber*, White mustard (*Sinapis alba*), White goosefoot (*Chenopodium album*), *Aster ageratoides* ssp. *Leiophyllus, Aquilaria agallocha*, Sudachi (*Citrus sudachi*), *Stevia* (*Stevia rebaudiana*), Liquorice (*Glycyrrhiza glabra* L.), Sage (*Salvia officinalis*), Savory (*Satureja* L.), Nettle (*Urtica dioica*), *Plantago major* L., St. John's wort (*Hypericum* perforatum), Valerian (*Valeriana officinalis*), Brown mustard (*Brassica juncea*), Dandelion (*Taraxacum officinale*), Elder (*Sambucus nigra*), *Petasites hybridus*, Horseradish (*Armoracia rusticana*), Bark/Tree branch/Root Bark of Ceylon Cinnamon (*Cinnamomum verum*), *Centella asiatica, Oenanthe javanica*, Cnidium Rhizome (*Cnidii Rhizoma*), *Swertia japonica* Makino, Buckwheat (*Fagopyrum esculentum*), Sorrel (*Rumex acetosa*), Rhubarb (*Rhei* Rhizoma), Daikon (*Raphanus sativus* var. *longipinnatus*), Oswego tea (*Monarda didyma*), Thyme (*Thymus*), *Formosa* lily (*Lilium formosanum*), Smartweed (*Persicaria*), *Cardamine scutata, Davilla rugosa*, Onion (*Allium cepa*), *Lilium nobilissimum*. Makino, Tarragon (*Artemisia dracunculus*), Chicory (*Cichorium intybus*), Chervil (*Anthriscus cerefolium*), Chives (*Allium schoenoprasum*), *Corda salicifolia*, Clove (*Syzygium aromaticum*), *Cassia angustifolia, Centella asiatica*, Tree onion (*Allium* x *proliferum*), *Reynoutria multiflora*, Daisy (*Bellis perennis*), Dill (*Anethum graveolens*), Devil's claw (*Harpagophytum*), *Farfugium japonicum*, Easter lily (*Lilium longiflorum*), Root of Devil's claw (*Harpagophytum*), *Rubus suavissimus*, Chili pepper (*Capsicum annuum*), Root of Japanese *angelica* (*Angelica acutiloba*), Star anise (Fruit of *Illicium verum*), Peach Kernel (Seed of *Prunus persica*), *Houttuynia cordata*, Blue Passion flower (*Passiflora caerulea*), *Rosa roxburghii*,

*Japanese ginseng* (*Panax japonicus*), leaves of *Eucommia ulmoides*, Tomato (*Solanum lycopersicum*), *Potentilla tormentilla, Rumex crispus*, Feverfew (*Tanacetum parthenium*), Jujube (*Ziziphus jujuba*), Wormwood (*Artemisia absinthium*), Garlic Chives (*Allium tuberosum*), Japanese red elder (*Sambucus sieboldiana*), Garlic (*Allium sativum*), Garden *nasturtium* (*Tropaeolum majus*), Saw palmetto (*Serenoa repens*), *Aster microcephalus* var. *ovatus, Allium macrostemon*, Welsh onion (*Allium fistulosum*), Basil (*Ocimum basilicum*), Mint (*Mentha*), *Lilium longiflorum*, Bush clover (*Lespedeza* sp.), *Alchemilla japonica*, Hajikami (*Zanthoxylum piperitum*), *Colocasia gigantea*, Parsley (*Petroselinum crispum*), Patchouli (*Patchouli*), Passion flower (*Passiflora*), Passion fruit (*Passiflora edulis*), Adlay (*Coix lacryma-jobi* var. *ma-yuen*), Vanilla, Habanero (*Capsicum chinense*), Roots of Paffia, Bell pepper (*Capsicum annuum grossum*), *Cyperus rotundus, Tribulus terrestris*, Jackfruit (*Artocarpus heterophyllus*), Jalapeno (*Capsicum annuum*), Bell pepper (*Capsicum annuum grossum*), *Prunus campanulata*, Hyssop (*Hyssopus officinalis*), Hinoki (*Chamaecyparis obtusa*), Long pepper (*Piper longum*), Balinese long pepper (*Piper retrofractum*), Sunflower (*Helianthus annuus*), *Elatostema japonicum, Allium monanthum, Lilium concolor, Lapsana apogonoides, Piri-piri* (*Capsicum frutescens* var red devil), *Areca catechu*, Bhut jolokia, Piper *kadsura*, Fenugreek seed, Fennel (*Foeniculum vulgare*), Butterbur (*Petasites japonicus*), Hyacinth bean (*Lablab purpureus*), Black cohosh (*Cimicifuga racemose*), Buntan (*Citrus maxima*), sponge gourd (*Luffa aegyptiaca*), Safflower (*Carthamus tinctorius*), *Gynura crepidioides*, Henna (*Lawsonia inermis*), Rue (*Ruta graveolens*), *Saposhnikovia divaricate, Paeonia suffruticosa*, Hop (*Humulus lupulus*), Ephedra, Marjoram (*Origanum majorana*), *Actinidia polygama, Machilus odoratissima, Pinus*, Japanese stone oak (*Lithocarpus edulis*), Mate (*Llex paraguariensis*), Madonna lily (*Lilium candidum*), Seed of Milk thistle (*Silybum marianum*), Seed of horse chestnut (*Aesculus hippocastanum*), Citrus, Root of *Bupleurum scorzonerifolium, Cryptotaenia japonica, Staphylea bumalda*, Myoga (*Zingiber mioga*), *Stauntonia hexaphylla*, Purple coneflower (*Echinacea purpurea*), *Nemacystus decipiens*, Willow (Salicaceae), *Hemerocaffis fulva*, Annona montana, Japanese mountain yam (*Dioscorea japonica*), Golden-rayed lily (*Lilium auratum*), *Allium thunbergii*, Yuzu (*Citrus junos*), Water spinach (*Ipomoea aquatica*), *Aster yomena*, Seed of Lychee (*Litchi chinensis*), Lime (*Citrus aurantiifolia*), *Allium chinense*, Lovage (*Levisticum officinale*), Lavender (*Lavandula*), Lamb's-ear (*Stachys byzantina*), Regal lily (*Lilium regale*), Leek (*Allium ampeloprasum*), *Pleioblastus linearis, Rubus okinawensis*, Unripe fruit of apple (*Malus pumila*), Flower of *Tilia cordata*, Rooibos (*Aspalathus linearis*), Rocket (*Eruca vesicaria* subsp. *Sativa*), Rhubarb, Borage (*Borago officinalis*), Lettuce (*Lactuca sativa*), Lemon (*Citrus limon*), Lemongrass (*Cymbopogon citratus*), Lemon thyme (*Thymus citriodorus*), *Lemon verbena* (*Lemon verbena*), Lemon balm (*Melissa officinalis*), Lemon myrtle (*Backhousia citriodora*), Forsythia, Rose hip (*Rosa canina*), flower bud of *Rosa damascena*, Rosemary (*Rosmarinus officinalis*), Rose red, Roselle (*Hibiscus sabdariffa*), Laurel (*Laurus nobilis*), Rocoto (*Capsicum pubescens*), *Aerides rosea*, Logwood (*Haematoxylum campechianum*), Tree onion (*Allium* x *proliferum*), Wasabi (*Eutrema japonicum*), Burnet (*Sanguisorba officinalis*), Chinese milkvetch (*Astragalus sinicus*), leaf of persimmon (*Diospyros kaki*), leaf of liquorice (*Glycyrrhiza glabra*), seed coat of black soybean (*Glycine max*), seed of black rice (*Oryza sativa* subsp. *javanica*), leaf of shell ginger (*Alpinia zerumbet*), *Lilium tenuifolium Fischer, Salix* sp., *Peucedanum japonicum* and their extracts; extracts of seaweeds such as *Gloiopeltis complanta, Gloiopeltis furcata*, and *Gloiopeltis tenax*; extracts of such as raw coffee bean, sweet potato shochu lees, mycelium of polypore (Polyporaceae) and mycelium of agaricus (*Agaricus subrufescens*): polyphenols such as resveratrol, quercetin, chlorogenic acid, anthocyanins, curcumin, kaempferol, catechins, flavonoids; carotenoids such as astaxanthin, β-cryptoxanthin, lycopene, fucoxanthin, lutein, crocetin, retinol, retinal, retinoic acid, β-carotene; pilocarpines such as pilocarpine hydrochloride; ephedrine, aspirin, sodium salicylate, insulin, adrenaline, acetylcholine, salicin, salicylic acid, choline salicylate, diflunisal, ethenzamide, mefenamic acid, diclofenac, sulindac, indomethacin, fervinac, etodolac, tolmetin, naptomen, ibuprofen, flurbiprofen, ketoprofen, naproxen, fenoprofen, oxaprozin, loxoprofen, zaltoprofen, ketorolac, piroxicam, ampiroxicam, meloxicam, lornoxicam, tenoxicam, celecoxib, valdecoxib, parecoxib sodium, tiaramide hydrochloride, tinoridine hydrochloride, epirizole, emorfazone, mepirizole, acetaminophen, phenylbutazone, oxyphenylbutazone, ketophenylbutazone, feprazone, sulfinpyrazone, antipyrine, sulpyrine, isopropylantipyrine, glycine, theanine, GABA, sake yeast, diphenhydramine hydrochloride, zolpidem tartrate, triazolam, zopiclone, eszopiclone, etizolam, brotizolam, rilmazafone hydrochloride, lormetazepam, flunitrazepam, estazolam, nitrazepam, quazepam, flurazepam hydrochloride, haroxazolam, ramelteon, suvorexant, mirtazapine, amitriptyline, mianserin, trazodone, risperidone, olanzapine, quetiapine, levomepromazine, chlorpromazine, alliin, allicin, capsaicin, dihydrocapsaicin, shogaol, gingerol, zingerone, zingiberene, piperine, sanshool, sanshoamide, geraniol, allyl isothiocyanate, phenethyl isothiocyanate, sinigrin, sinalbin, sulforaphane glucosinolate, equol, isoflavone, L-tyrosine, L-Phenylalanine, L-Tryptophan, 1,3,5-trihydroxybenzene, 3,4-dihydroxyphenylacetic acid, L-3,4-dihydroxyphenylalanine, 4-(2-aminoethyl) benzene-1,2-diol, noradrenaline, adrenaline, 5-hydroxytryptamine, caffeic acid, ifenprodil, α-lipoic acid, 4-hydroxychalcone, ergothioneine, resveratrol, carnosine, carnitine, salicylic acid hydrobromide, sinapinic acid, ferulic acid, cinnamic acid, tocopheryl nicotinate, α -tocopherol, β-tocopherol, γ-tocopherol, δ-tocopherol, α-tocotrienol, β-tocotrienol, γ-tocotrienol, δ-tocotrienol, nicotinamide, proanthocyanidin, hydrolyzable tannins, catechol, chlorogenic acids (such as chlorogenic acid, isochlorogenic acid, neochlorogenic acid, cryptochlorogenic acid and caffeoylquinic acid), cyanidin, leucocyanidin, prunin, procyanidol oligomer, glucosyl rutin, glucosyl naringin, lutein, astaxanthin, delphinidin, delphinidin glucoside, berry extract, bilberry extract, prune extract, vitamin A, vitamin B2, vitamin B6, vitamin B12, vitamin E, docosahexaenoic acid, eicosapentaenoic acid, β-carotene, α-lipoic acid, lecithin, zinc, selenium, L-glutathione, N-acetyl-L-cysteine, lycopene, sesamin, zeaxanthin, taurine, Lactic acid bacteria (Lactobacillales), coenzyme Q10, green tea extract, *Ginkgo biloba* extract, grape seed extract, pine bark extract, and their derivatives.

The agent for adjusting hardness of a lens of an eye of the present invention may be in any form, but in a preferred embodiment it may be in a solid form, granulated form, powder form, suspension form, paste form, jelly form, capsule form, and liquid form, such as lozenges, liver oil drops, complex vitamins, mouth fresheners, mouth fragrant tablets, oral and tube feedings, and oral medications. It may be also formulated into various compositions in the aforementioned forms. The method for making the agent of the present invention into the aforementioned forms and the method for formulating the agent of the present invention into the compositions in the aforementioned forms may be any method and not be limited to a specific method. For example, one or more known methods such as mixing, kneading, blending, adding, dissolving, immersing, permeating, spreading, coating, spraying, and injecting may be appropriately used in the process until the composition in those forms is made. The amount of glycosyl hesperetin to be contained as an active ingredient in the agent for adjusting hardness of a lens of an eye of the present invention may be any amount as long as the desired effect can be achieved.

As explained above, by the agent for adjusting hardness of a lens of an eye in accordance with one embodiment of the present invention, hardening of the lens, in particular hardening of the lens with aging may be inhibited and/or the once hardened lens may be softened. Accordingly, in another aspect of the present invention, a method for adjusting hardness of a lens of an eye, in more detail, a method for inhibiting hardening of a lens of an eye and a method for softening a lens of an eye, which uses glycosyl hesperetin as an active ingredient may be also provided. In these methods, the preferred composition, production method, content, ingestion amount of glycosyl hesperetin used as an active ingredient, and combination with other ingredients are the same as those described for the agent for adjusting hardness of a lens of an eye. The method for adjusting hardness of a lens of an eye, which uses glycosyl hesperetin as an active ingredient in accordance with one embodiment of the present invention may be advantageously used as a method for preventing, alleviating, and improving symptoms such as poor focus or decline of near visual acuity, such as presbyopia, caused by aging and various diseases, and further preventing, alleviating, and improving various symptoms caused by poor focus or decline of near visual acuity, such as presbyopia, including eye fatigue, blurred vision, eye pain, dry eye, stiff necks, headache, neck/shoulder/arm/back pain or dullness, numbness in limbs, dizziness, insomnia, increased stress, decreased activity, weight loss, decreased muscle strength, decreased muscle mass, decreased bone strength, decreased bone density, decreased vitality, decreased cognitive function, and depression; increased fall risk, etc., and various diseases such as eye diseases with aging including cataract, glaucoma, retinal detachment, retinopathy, maculopathy, choroidal neovascularization, posterior staphyloma, optic neuropathy, etc.

The present invention is explained in more detail by the below described experiments.

Experiment 1: Effect of Administration of Glycosyl Hesperetin on Hardening of the Lens of Rats Induced by Sodium Selenite By subcutaneous injection of sodium selenite, hardening of the lens was induced in rats, and these rats with induced hardening of the lens were used as model animals. Samples containing glycosyl hesperetin or control samples were administered to the rats and the hardness of the lens was measured.

Experiment 1-1: Preparation of Glycosyl Hesperetin

Glycosyl hesperetin was prepared according to the method described in Example 1 of the International Publication WO2015/133483. In detail, 4 parts by mass of 1 N aqueous sodium hydroxide solution was heated to 80° C. One (1) part by mass of hesperidin and 7 parts by mass of dextrin (DE20) were added to the heated aqueous sodium hydroxide solution and dissolved by stirring for 30 mins. The pH of the solution was adjusted to 9.0 and then 30 units/g-dextrin of cyclodextrin glucanotransferase derived from *Geobacillus stearothermophilus* Tc-91 strain (deposit number: FERM BP-11273, National Institute of Technology and Evaluation, NITE Patent Microorganisms Depositary (NPMD)) was added and subjected to an enzymatic reaction for 18 hours while keeping the pH at 6.9 and the temperature at 50° C. After inactivation of the enzyme remaining in the resulting enzymatic reaction solution by heat, the enzymatic reaction solution was added with glucoamylase (product name "GLUCOZYME", Nagase ChemteX Corporation, Osaka, Japan) in an amount of 100 units per gram solids of the enzymatic reaction solution and then was subjected to an enzymatic reaction for 5 hours while keeping the pH at 5.0 and the temperature at 55° C. so that α-glucosyl hesperidin was formed. The resulting enzymatic reaction solution was then heated to inactivate the enzyme remaining in the solution and the solution was filtered. The obtained filtrate was fed to a column packed with a porous synthetic adsorbent (product name "DIAION HP-10", sold by Mitsubishi Chemical Corporation, Tokyo, Japan) at a space velocity (SV) of 2. After washing the column with purified water, the column was fed with an aqueous ethanol solution and the concentration of ethanol in the aqueous ethanol solution was increased in a stepwise manner, to collect fractions comprising α-glucosyl hesperidin. The collected fractions were concentrated in vacuo and pulverized to obtain a pale yellow glycosyl hesperetin powder. The thus obtained glycosyl hesperetin powder contained 80.0% by mass of α-glucosyl hesperidin, 12.3% by mass of hesperidin, and 7.7% by mass of other ingredients. The composition of the glycosyl hesperetin powder was equivalent to that of a commercially available glycosyl hesperetin (product name "Hayashibara Hesperidin 5", sold by Hayashibara Co., Ltd., Okayama, Japan).

Experiment 1-2: Preparation of Test Sample

Two hundred (200) mg of the glycosyl hesperetin powder obtained in Experiment 1-1 was dissolved in 10 mL of phosphate buffered saline (PBS: 130 mM sodium chloride, 3 mM potassium chloride, 10 mM sodium hydrogen phosphate, 2 mM potassium dihydrogen phosphate, pH 7.4) to obtain test sample 1. As a control sample, PBS was used.

Experiment 1-3: Short-Term Dosing Study of Glycosyl Hesperetin

Male Sprague-Dawley (SD) rats of 13 days old were divided into the following four groups: test group 1 (group injected with PBS and administered with control sample), test group 2 (group injected with PBS and administered with test sample 1), test group 3 (group injected with sodium selenite and administered with control sample), and test group 4 (group injected with sodium selenite and administered with test sample 1). Each group consisted of 3 mice. Test group 2 and 4 were given 0.2 mL of test sample 1 obtained in Experiment 1-2 (10 mL/kg-body weight, equivalent to a dose of 200 mg/kg-body weight in terms of a dose of glycosyl hesperetin) orally with a gastric tube once a day for 3 consecutive days. Meanwhile, test group 1 and 3 were given 0.2 mL of PBS orally with a gastric tube once a day for 3 consecutive days. After 4 hours of the first administration with a gastric tube, test groups 3 and 4 were given 0.35 mg/mL of sodium selenite (FUJIFILM Wako Pure Chemical Corporation, Osaka, Japan) in an amount of 20

μmol/kg-body weight via subcutaneous injection to induce hardening of the lens. Test group 1 and 2 were given PBS instead of sodium selenite via subcutaneous injection. When the rats became 17 days old, the lens of the rats were collected and the hardness of the lens was measured promptly. Breeding condition including feed (product name "CE-2", CLEA Japan Inc., Tokyo, Japan), temperature (23±5° C.), humidity (50±10%), lighting (light period 12 hours, dark period 12 hours), etc. was the same for all test groups.

Evaluation Items and Evaluation Method

The hardness of the lens of 17-day-old rats for each test group was evaluated. The evaluation of the hardness of the lens was conducted using an elasticity measuring instrument (SoftMeasure HG1003-SL, Horiuchi Electronics Co., Ltd., Tokyo, Japan). In detail, the lens was removed immediately after euthanasia and the removed lens was placed on the measurement table with the medial side of the eyeball down and so that the lens was parallel to the measurement table. A flat indenter with a diameter of 12 mm was aligned with the center of the lens, and then was lowered vertically so that the lens was applied with a pressure at an indentation speed of 0.1 mm/sec. During indentation, the load and the dents of the lens were measured, and the load required for producing 15% dents of the lens was used as an indicator of the hardness of the lens. The mean of the load required for producing 15% dents of the lens of each test group and its standard error were shown in Table 1.

Statistical Analysis

Measured values were expressed as mean±standard error (SE). Statistical analysis was performed using SPSS software version 24 (IBM Japan, Ltd., Tokyo, Japan). After one-way analysis of variance (one-way ANOVA), Tukey's multiple comparison test was performed. A significance level (p value) of less than 0.05 (less than 5% risk) was judged to be significant.

TABLE 1

| | | Load (mN) |
|---|---|---|
| Test Group 1 | PBS injection + control sample administration group | 4.0 ± 0.2* |
| Test Group 2 | PBS injection + test sample 1 administration group | 3.8 ± 0.4 |
| Test Group 3 | sodium selenite injection + control sample administration group | 7.5 ± 0.6 |
| Test Group 4 | sodium selenite injection + test sample 1 administration group | 3.8 ± 0.4* |

*$p < 0.05$ vs Test Group 3 (sodium selenite injection + control sample administration group)

As shown in Table 1, the mean of the load required for producing 15% dents of the lens (hereinafter simply referred to as "the load" unless otherwise specified), which is an indicator of the hardness of the lens, was 4.0±0.2 mN in test group 1, but the mean of the load was 7.5±0.6 mN in test group 3, which was apparently higher than that in test group 1, indicating that hardening of the lens was induced by the sodium selenite injection. In contrast, the mean of the load was remarkably as low as 3.8±0.4 mN in test group 4, indicating that the administration of test sample 1 containing glycosyl hesperetin significantly inhibited hardening of the lens induced by the injection of sodium selenite. Meanwhile, there was no significant difference between the load of test group 2 and that of test group 1.

The above results confirm that the hardening of the lens induced by the injection of sodium selenite is inhibited by intake of glycosyl hesperetin. This result indicates that glycosyl hesperetin has the effect of inhibiting hardening of the lens and is useful as an active ingredient of the agent for adjusting hardness of a lens on an eye.

Experiment 2: Effect of Administration of Low-Concentration Glycosyl Hesperetin on Hardening of the Lens of Rats Induced by Sodium Selenite In Experiment 1, the effect of inhibiting hardening of the lens was observed in test group 4, which were administered with glycosyl hesperetin at a dose of 200 mg/kg-body weight per day for 3 consecutive days. Since the effect of inhibiting hardening of the lens by the short-term administration of glycosyl hesperetin was confirmed in Experiment 1, a sample containing glycosyl hesperetin at a lower concentration than Experiment 1 was prepared and whether the effect of inhibiting hardening of the lens is obtained by administration of glycosyl hesperetin at lower dose or not was investigated.

Experiment 2-1: Preparation of Test Sample

Two hundred (200) mg of the glycosyl hesperetin powder obtained in Experiment 1-1 was dissolved in 2000 mL and 200 mL of PBS to obtain test sample 2 and test sample 3, respectively. As a control sample, PBS was used.

Experiment 2-2: Short-Term Dosing Study of Glycosyl Hesperetin—Part 2—

Male SD rats of 13 days old were divided into the following four groups: test group 5 (group injected with PBS and administered with control sample), test group 6 (group injected with sodium selenite and administered with control sample), test group 7 (group injected with sodium selenite and administered with test sample 2), and test group 8 (group injected with sodium selenite and administered with test sample 3). Each group consisted of 3 mice. Test group 7 was given 0.2 mL of test sample 2 obtained in Experiment 2-1 (10 mL/kg body weight, equivalent to a dose of 1 mg/kg body weight in terms of a dose of glycosyl hesperetin) orally with a gastric tube once a day for 3 consecutive days. Test group 8 was given 0.2 mL of test sample 3 obtained in Experiment 2-1 (10 m L/kg body weight, equivalent to a dose of 10 mg/kg body weight in terms of a dose of glycosyl hesperetin) orally with a gastric tube once a day for 3 consecutive days. Meanwhile, test groups 5 and 6 were given 0.2 mL of PBS orally with a gastric tube once a day for consecutive 3 days. After 4 hours of the first administration with a gastric tube, test groups 6 to 8 were given 0.35 mg/mL of sodium selenite (FUJIFILM Wako Pure Chemical Corporation, Osaka, Japan) in an amount of 20 μmol/kg-body weight via subcutaneous injection to induce hardening of the lens. Test group 5 was given PBS instead of sodium selenite via subcutaneous injection. When the rats became 17 days old, the lens of the rats were collected and the hardness of the lens was measured promptly. The same breeding condition as described in Experiment 1 was used.

Evaluation Items and Evaluation Method

The hardness of the lens of 17-day-old rats for each test group was evaluated. The evaluation of the hardness of the lens was conducted in the same manner as described in Experiment 1-3. As an indicator of the hardness of the lens after intake of each sample against hardening of the lens during breeding period, the mean of the load required for producing 15% dents of the lens and its standard error were obtained and shown in Table 2.

Statistical Analysis

Measured values were expressed as mean±standard error (SE), and statistical analysis was performed in the same manner as described in Experiment 1-3.

TABLE 2

| | | Load (mN) |
|---|---|---|
| Test Group 5 | PBS injection + control sample administration group | 2.6 ± 0.3** |
| Test Group 6 | sodium selenite injection + control sample administration group | 7.5 ± 0.6 |
| Test Group 7 | sodium selenite injection + test sample 2 administration group | 4.5 ± 0.5* |
| Test Group 8 | sodium selenite injection + test sample 3 administration group | 3.4 ± 0.4** |

*p < 0.05 vs Test Group 6 (sodium selenite injection + control sample administration group)
*p < 0.01 vs Test Group 6 (sodium selenite injection + control sample administration group)

As shown in Table 2, the mean of the load required for producing 15% dents of the lens, which is an indicator of the hardness of the lens, was 2.6±0.3 mN in test group 5, but the mean of the load was 7.5±0.6 mN in test group 6, which was apparently higher than that in test group 5, indicating that hardening of the lens was induced by the sodium selenite injection. In contrast, the mean of the load was 4.5±0.5 mN in test group 7 and was 3.4±0.4 mN in test group 8, which were significantly lower compared to a group administered with control sample (test group 6). These results indicate that the administration of test sample 2 or 3 containing glycosyl hesperetin remarkably inhibited hardening of the lens induced by the injection of sodium selenite. Meanwhile, the mean of the load measured for test group 7 and 8 were in the similar level as that measured for test group 4 in Experiment 1-3, which were administered with glycosyl hesperetin at a dose of 200 mg/kg-body weight per day.

The above results indicate that hardening of the lens induced by the injection of sodium selenite is effectively inhibited by intake of glycosyl hesperetin even at a dose of 1 mg/kg-body weight (test group 7) or 10 mg/kg-body weight (test group 8) of glycosyl hesperetin per day, which are much lower compared to the dose used for test group 4 in Experiment 1. This result indicates that glycosyl hesperetin has an excellent effect of inhibiting hardening of the lens and is useful as an active ingredient of the agent for adjusting hardness of a lens of an eye.

Experiment 3: Effect of Long-Term Intake of Glycosyl Hesperetin on Hardening of the Lens with Aging In Experiments 1 and 2, the effect of inhibiting hardening of the lens by a short-term administration of glycosyl hesperetin was confirmed. Therefore, as a natural aging model experiment, mice were bred for a long-term while being fed with a test sample containing glycosyl hesperetin or a control sample, and the hardness of the lens after the long-term breeding was measured.

Experiment 3-1: Preparation of Test Samples

The glycosyl hesperetin powder obtained in Experiment 1-1 was dissolved in tap water to a concentration of 1% by mass or 2% by mass to obtain test sample 4 and test sample 5, respectively. As a control sample, tap water was used.

Experiment 3-2: Long-Term Dosing Study of Glycosyl Hesperetin

Male C57BL/6JJ mice of 9 weeks old were divided into the following six groups: test group 9 (control sample ingestion group), test group 10 (test sample 4 ingestion group) and test group 11 (test sample 5 ingestion group) as groups administered with samples for a period of 16 weeks; and test group 12 (control sample ingestion group), test group 13 (test sample 4 ingestion group) and test group 14 (test sample 5 ingestion group) as groups administered with samples for a period of 28 weeks. Each group consisted of 6 mice. Test groups 10 and 13 were allowed to ingest test sample 4 obtained in Experiment 3-1; test groups 11 and 14 were allowed to ingest test sample 5 obtained in Experiment 3-1; and test groups 9 and 12 were allowed to ingest control sample by the free-drinking method, in which mice were allowed to drink as much water as they wanted at any time. The lenses were collected when the mice became 25 weeks old for test groups 9 to 11 (groups administered with samples for a period of 16 weeks) and when the mice became 37 weeks old for test groups 12 to 14 (groups administered with samples for a period of 28 weeks), and the hardness of the lens was measured promptly after collection. Breeding condition including feed (product name “CE-2”, CLEA Japan Inc., Tokyo, Japan), temperature (23±5° C.), humidity (50±10%), lighting (light period 12 hours, dark period 12 hours), etc. was the same for all test groups.

Evaluation Items and Evaluation Method

Figure 2:
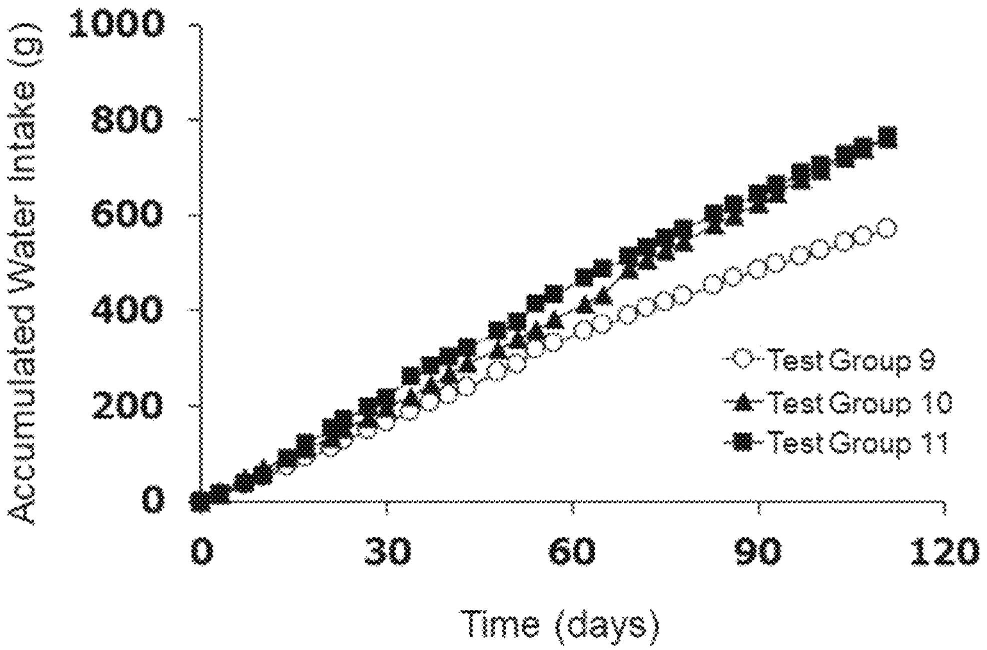
FIG. 2 The figure showing the total amount of water intake by test mice fed with a test sample containing glycosyl hesperetin or a control sample for 16 weeks.
Figure 3:
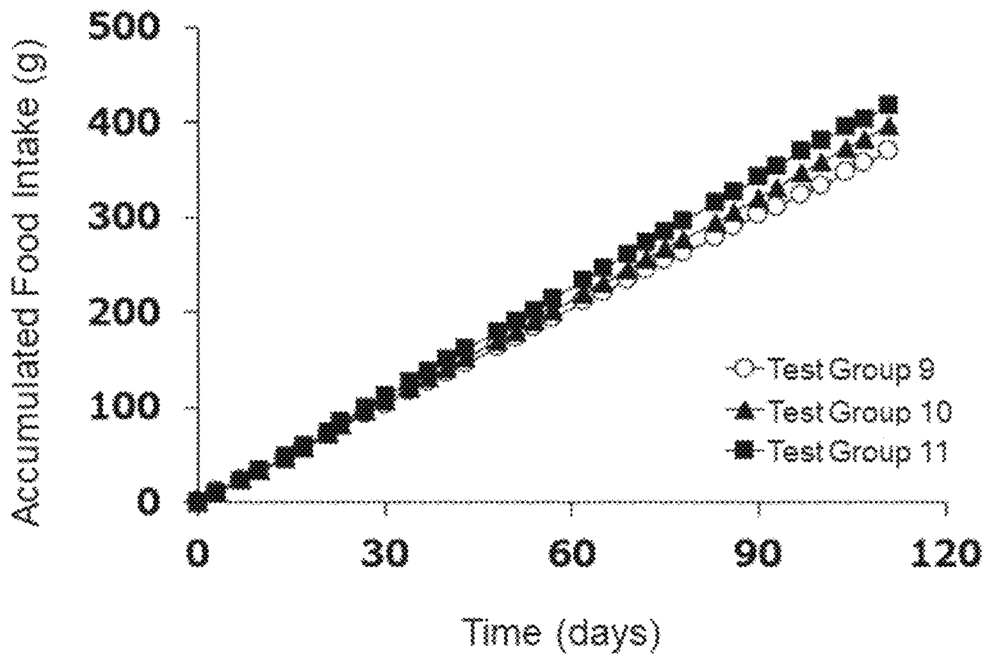
FIG. 3 The figure showing the total amount of food intake by test mice fed with a test sample containing glycosyl hesperetin or a control sample for 16 weeks.
Figure 4:
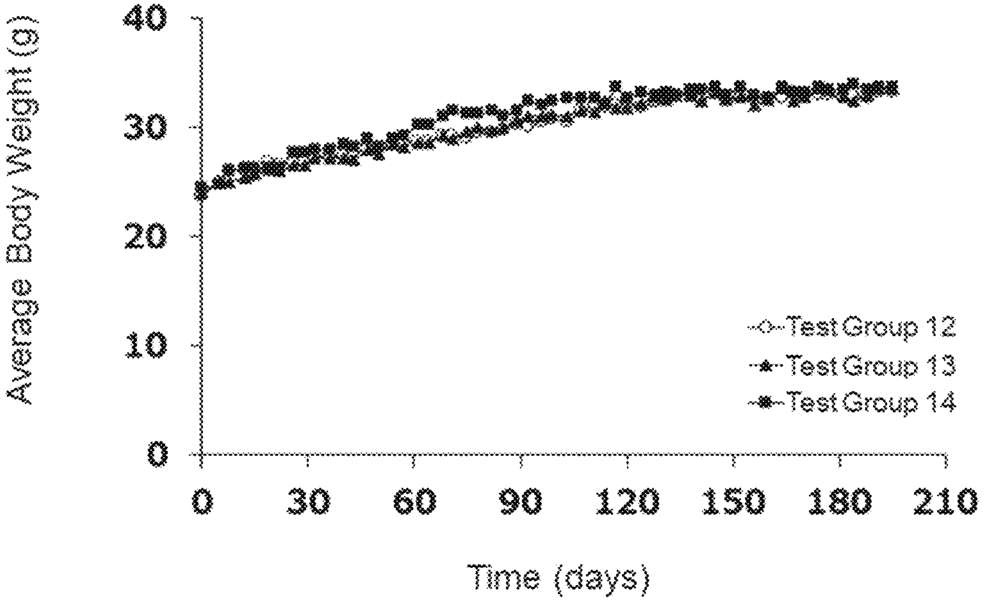
FIG. 4 The figure showing the change over time in body weight of test mice fed with a test sample containing glycosyl hesperetin or a control sample for 28 weeks.
Figure 5:
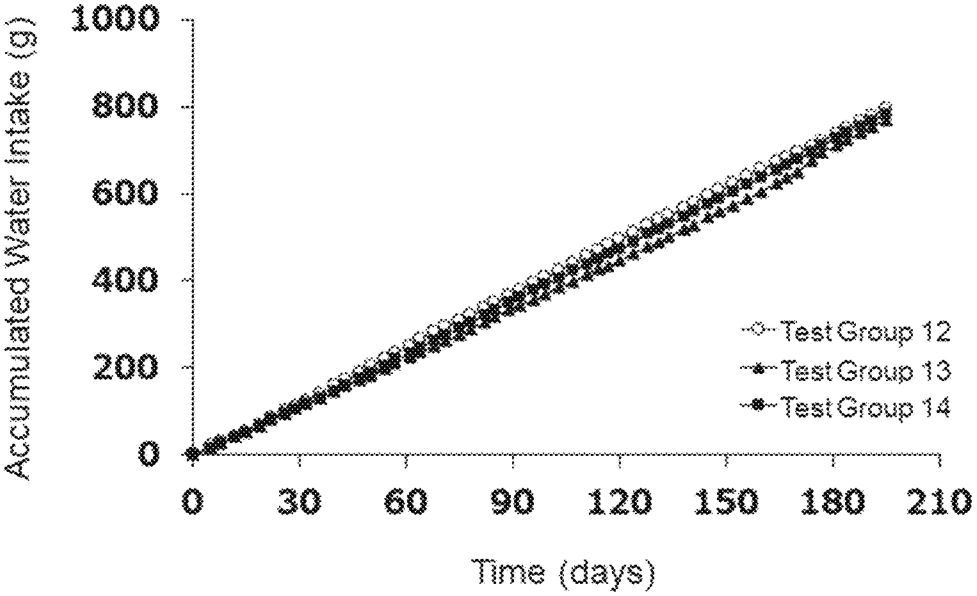
FIG. 5 The figure showing the total amount of water intake by test mice fed with a test sample containing glycosyl hesperetin or a control sample for 28 weeks.
Figure 6:
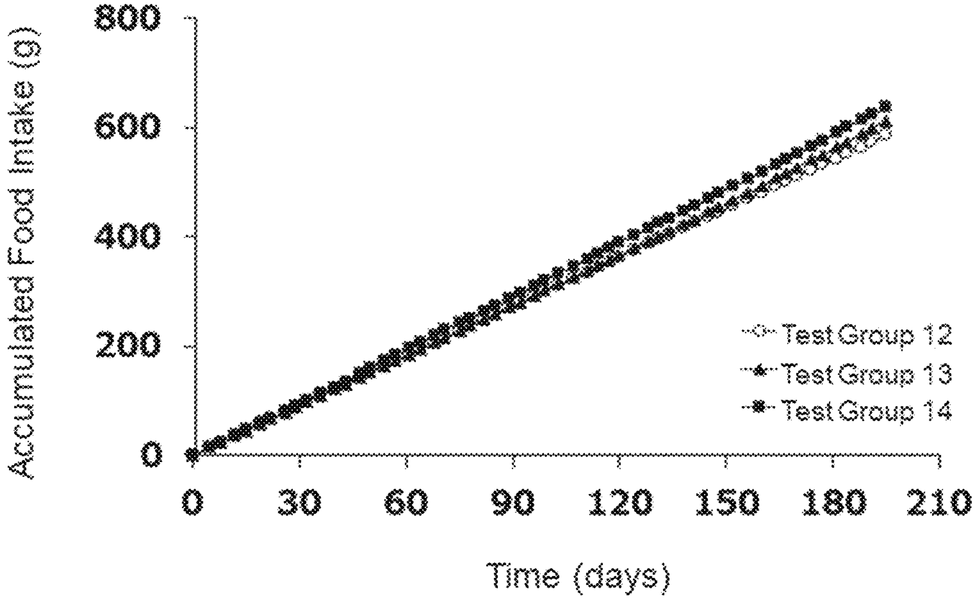
FIG. 6 The figure showing the total amount of food intake by test mice fed with a test sample containing glycosyl hesperetin or a control sample for 28 weeks.

The hardness of the lens of 9-week-old mice before taking samples and the hardness of the lens of 25-week-old and 37-week-old mice of each test group were evaluated. The measurement of the hardness of the lens was conducted in the same manner as described in Experiment 1-3. As an indicator of the lens hardness after intake of each sample against hardening of the lens with aging during a long-term breeding period, the mean of the load required for producing 15% dents of the lens and its standard error were obtained and shown in Table 3. In addition, from the start of the experiment to the time when the lens was collected, the body weight, the amount of water intake, and the amount of food intake were monitored every day for each group. For groups administered with samples for a period of 16 weeks (test groups 9 to 11), the time-course changes in the average body weight, the average accumulated water intake, and the average accumulated food intake were shown in FIG. 1, FIG. 2 and FIG. 3, respectively. For groups administered with samples for a period of 28 weeks (test groups 12 to 14), the time-course changes in the average body weight, the average accumulated water intake, and the average accumulated food intake were shown in FIG. 4, FIG. 5 and FIG. 6, respectively.

Statistical Analysis

Measured values were expressed as mean±standard error (SE), and statistical analysis was performed in the same manner as described in Experiment 1-3.

TABLE 3

| | | Load (mN) | | |
|---|---|---|---|---|
| | | 9-week-old (Before administration) | 25-week-old (Administration for 16 weeks) | 37-week-old (Administration for 28 weeks) |
| Test Group 9 | Control sample ingestion group | 10.0 ± 1.1 | 11.0 ± 1.6 | — |
| Test Group 10 | Test sample 4 ingestion group | | 8.9 ± 0.7* | — |
| Test Group 11 | Test sample 5 ingestion group | | 7.8 ± 3.0 | — |
| Test Group 12 | Control sample ingestion group | | — | 11.6 ± 0.4 |
| Test Group 13 | Test sample 4 ingestion group | | — | 7.3 ± 0.8* |
| Test Group 14 | Test sample 5 ingestion group | | — | 8.0 ± 0.4* |

*$p < 0.05$ vs 9-week-old (Before administration)

The average body weight, the average accumulated water intake, and the average accumulated food intake for each group were shown in FIG. 1 to FIG. 6. Although a slight variation in the accumulated water intake was observed in the groups ingesting samples for a period of 16 weeks, it was judged that the variation would not affect the later described result.

As shown in Table 3, the mean of the load required for producing 15% dents of the lens, which is an indicator of the hardness of the lens, was 10.0±1.1 mN for 9-week-old mice before administration of the samples, but the mean of the load was increased to 11.0±1.6 mN for 25-week-old mice of the group that ingested control sample (test group 9), indicating hardening of the lens with aging. In contrast, the mean of the load was 8.9±0.7 mN and 7.8±3.0 mN for 25-week-old mice of test group 10 which ingested test sample 4 for a period of 16 weeks and test group 11 which ingested test sample 5 for a period of 16 weeks, respectively, which were significantly lower compared to the mean of the load (11.0±1.6 mN) obtained for test group 9 in which hardening of the lens with aging was observed. This result indicates that hardening of the lens with aging was inhibited in test groups 10 and 11, which were administered with test sample 4 and test sample 5, respectively, for a period of 16 weeks. Surprisingly, the mean of the load obtained for test group 10 and test group 11 was significantly lower even compared to the mean of the load (10.0±1.1 mN) obtained for the 9-week-old mice before administration of samples. This result indicates that not only hardening of the lens with aging was inhibited but also the lens was softened by administration of test sample 4 or test sample 5 containing glycosyl hesperetin.

Furthermore, as shown in Table 3, the mean of the load required for producing 15% dents of the lens, which is an indicator of the hardness of the lens, was 10.0±1.1 mN for 9-week-old mice before administration of the samples, but the mean of the load was increased to 11.6±0.4 mN for 37-week-old mice of the group that ingested control sample (test group 12), indicating further hardening of the lens with aging compared to the 25-week-old mice of the group that ingested control sample. In contrast, the mean of the load was 7.3±0.8 mN and 8.0±0.4 mN for 37-week-old mice of test group 13 which were administered with test sample 4 for a period of 28 weeks and test group 14 which were administered with test sample 5 for a period of 28 weeks, respectively, which were significantly lower compared to the mean of the load (11.6±0.4 mN) obtained for test group 12 in which hardening of the lens with aging was observed. This result indicates that hardening of the lens with aging was inhibited in test groups 13 and 14, which were administered with test sample 4 and test sample 5, respectively, for a period of 28 weeks. Surprisingly, the mean of the load obtained for test group 13 and test group 14 was remarkably lower even compared to the mean of the load (10.0±1.1 mN) obtained for the 9-week-old mice before administration of samples. This result indicates that not only hardening of the lens with aging was inhibited but also the lens was softened by administration of test sample 4 or test sample 5 containing glycosyl hesperetin.

As above, it was confirmed that the hardening of the lens with aging is inhibited by intake of glycosyl hesperetin. This result indicates that glycosyl hesperetin has the effect of inhibiting hardening of the lens and is useful as an active ingredient of the agent for adjusting hardness of a lens of an eye. Furthermore, it was confirmed that intake of glycosyl hesperetin not only inhibits the hardening of the lens but also decreases the hardness of the lens compared to the 9-week-old mice before administration of the samples. This result indicates that glycosyl hesperetin has the effect of softening the lens and is useful as an active ingredient of the agent for adjusting hardness of a lens of an eye.

Experiment 4: Effect of Long-Term Intake of Glycosyl Hesperetin on Hardening of the Lens with Aging—Part 2—

In Experiment 3, the effect of inhibiting hardening of the lens and the effect of softening the lens by a long-term administration of glycosyl hesperetin was confirmed. Therefore, a sample containing glycosyl hesperetin at a lower concentration than Experiment 3 was prepared, and the hardness of the lens of mice after breeding the mice for a shorter period than in Experiment 3 while feeding the mice with test sample containing glycosyl hesperetin or control sample was measured.

Experiment 4-1: Preparation of Test Sample

The glycosyl hesperetin powder obtained in Experiment 1-1 was dissolved in tap water to a concentration of 0.1% by mass to obtain test sample 6. As a control sample, tap water was used.

Experiment 4-2: Long-Term Dosing Study of Glycosyl Hesperetin

Male C57BL/6JJ mice of 9 weeks old were divided into the following four groups: test group 15 (control sample ingestion group) and test group 16 (test sample 6 ingestion group) as groups administered with samples for a period of 10 weeks; and test group 17 (control sample ingestion group) and test group 18 (test sample 6 ingestion group) as groups administered with samples for a period of 15 weeks. Each group consisted of 6 mice. Test groups 16 and 18 were allowed to ingest test sample 6 obtained in Experiment 4-1, while test groups 15 and 17 were allowed to ingest control sample by the free-drinking method, in which mice were allowed to drink as much water as they wanted at any time. The lenses were collected when the mice became 19 weeks old for test groups 15 and 16 (groups administered with the samples for a period of 10 weeks) and when the mice became 24 weeks old for test groups 16 and 17 (groups administered with the samples for a period of 15 weeks), and the hardness of the lens was measured promptly after collection. The same breeding condition as described in Experiment 3 was used.

Evaluation Items and Evaluation Method

Figure 7:
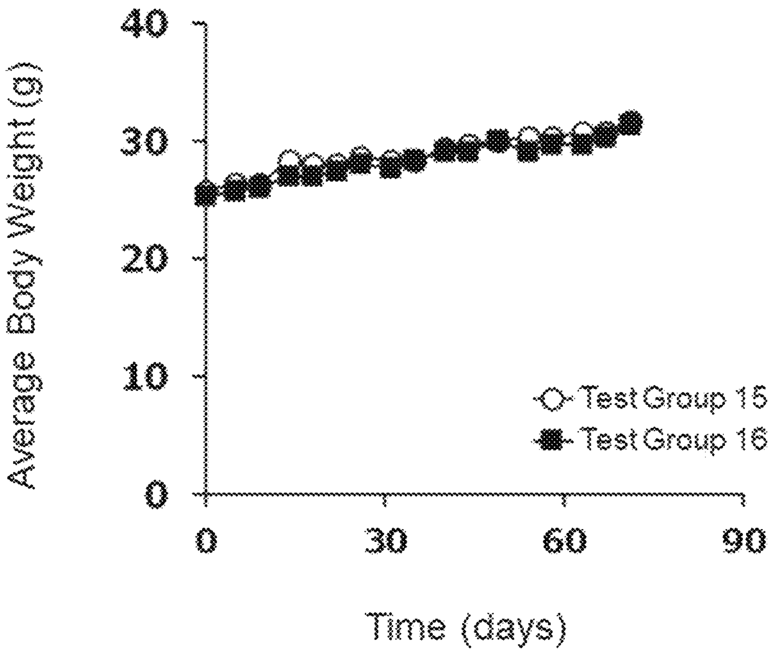
FIG. 7 The figure showing the change over time in body weight of test mice fed with a test sample containing glycosyl hesperetin or a control sample for 10 weeks.
Figure 8:
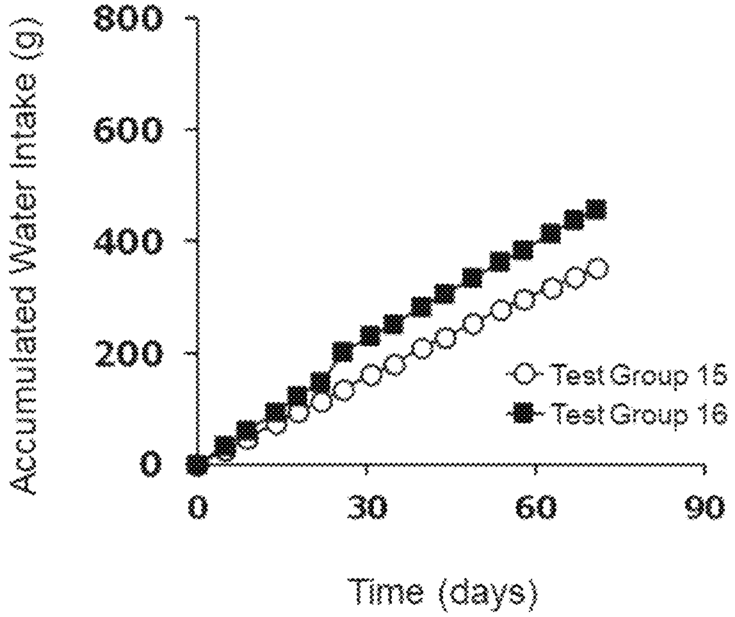
FIG. 8 The figure showing the total amount of water intake by test mice fed with a test sample containing glycosyl hesperetin or a control sample for 10 weeks.
Figure 9:
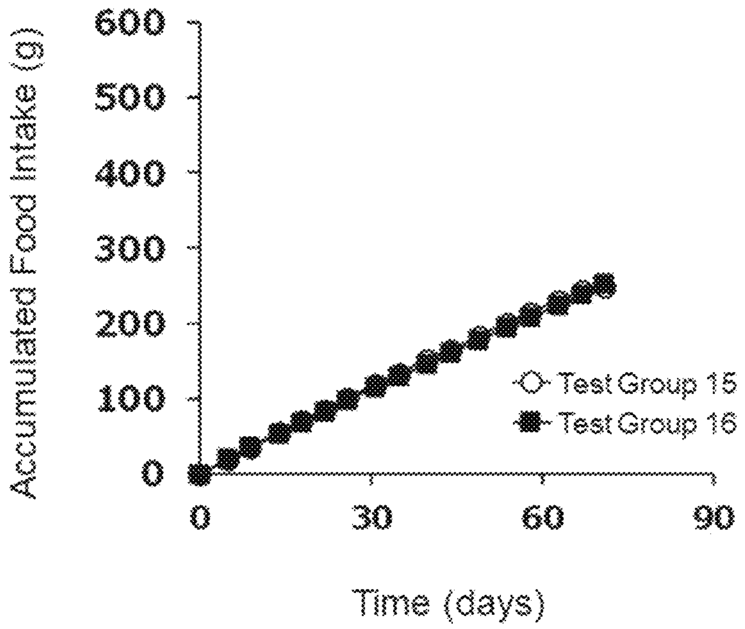
FIG. 9 The figure showing the total amount of food intake by test mice fed with a test sample containing glycosyl hesperetin or a control sample for 10 weeks.
Figure 10:
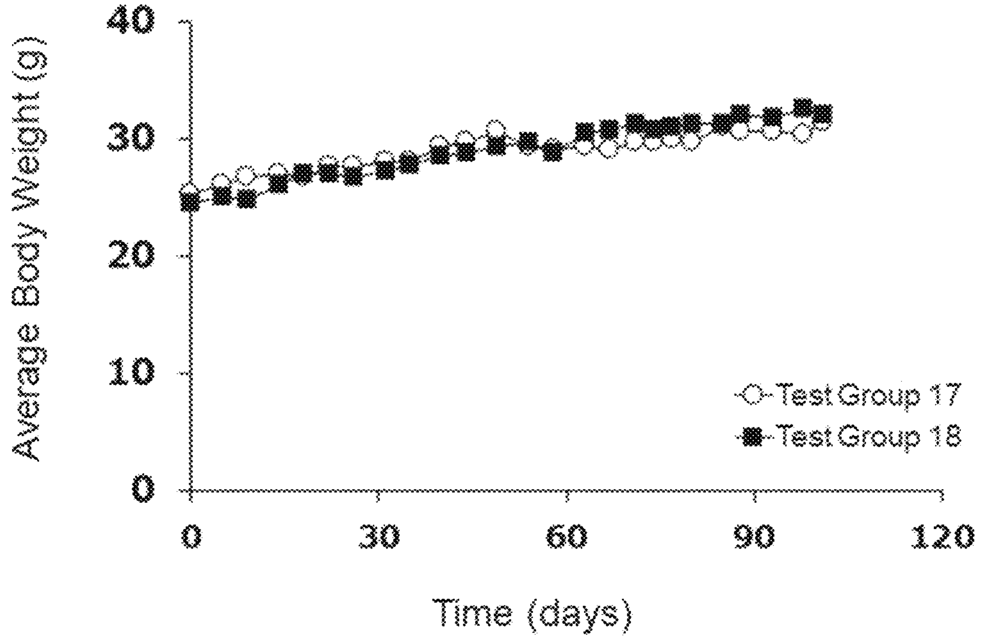
FIG. 10 The figure showing the change over time in body weight of test mice fed with a test sample containing glycosyl hesperetin or a control sample for 15 weeks.
Figure 11:
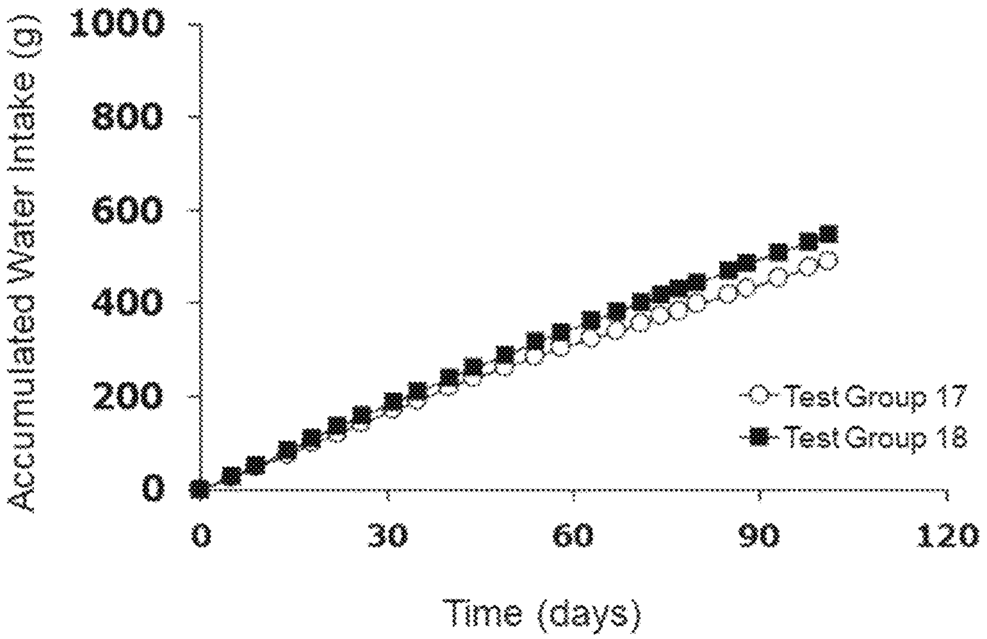
FIG. 11 The figure showing the total amount of water intake by test mice fed with a test sample containing glycosyl hesperetin or a control sample for 15 weeks.
Figure 12:
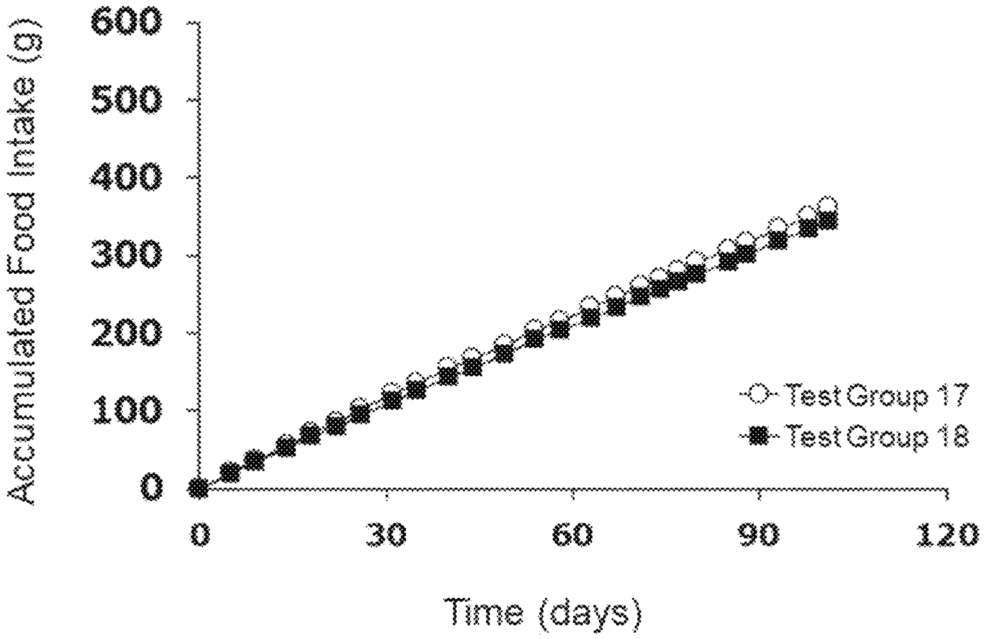
FIG. 12 The figure showing the total amount of food intake by test mice fed with a test sample containing glycosyl hesperetin or a control sample for 15 weeks.

The hardness of the lens of 9-week-old mice before taking samples and the hardness of the lens of 19-week-old and 24-week-old mice of each test group after taking each sample were evaluated. The measurement of the hardness of the lens was conducted in the same manner as described in Experiment 1-3. As an indicator of the lens hardness after intake of each sample against hardening of the lens with aging during a long-term breeding period, the mean of the load required for producing 15% dents of the lens and its standard error were shown in Table 4. In addition, from the start of the experiment to the time when the lens was collected, the body weight, the amount of water intake, and the amount of food intake were monitored every day for each group. For groups administered with samples for a period of 10 weeks (test groups 15 and 16), the time-course changes in the average body weight, the average accumulated water intake, and the average accumulated food intake were shown in FIG. 7, FIG. 8 and FIG. 9, respectively. For groups administered with samples for a period of 15 weeks (test groups 17 and 18), the time-course changes in the average body weight, the average accumulated water intake, and the average accumulated food intake were shown in FIG. 10, FIG. 11 and FIG. 12, respectively.

Statistical Analysis

Measured values were expressed as mean±standard error (SE), and statistical analysis was performed in the same manner as described in Experiment 3.

TABLE 4

| | | Load (mN) | | |
|---|---|---|---|---|
| | | 9-week-old (Before administration) | 19-week-old (Administration for 10 weeks) | 24-week-old (Administration for 15 weeks) |
| Test Group 15 | Control sample ingestion group | 10.0 ± 1.0 | 10.7 ± 1.3 | — |
| Test Group 16 | Test sample 6 ingestion group | | 9.0 ± 0.7 | — |
| Test Group 17 | Control sample ingestion group | | — | 10.7 ± 0.5 |
| Test Group 18 | Test sample 6 ingestion group | | — | 7.6 ± 1.3 |

The average body weight, the average accumulated water intake, and the average accumulated food intake for each group were shown in FIG. 7 to FIG. 12. Although a slight variation in the accumulated water intake was observed in the groups administered with samples for a period of 10 weeks, it was judged that the variation would not affect the later described result.

As shown in Table 4, the mean of the load required for producing 15% dents of the lens, which is an indicator of the hardness of the lens, was 10.0±1.0 mN for 9-week-old mice before administration of the samples, but the mean of the load was increased up to 10.7±1.3 mN for 19-week-old mice of the group that ingested control sample (test group 15), indicating hardening of the lens with aging. In contrast, the mean of the load was 9.0±0.7 mN for 19-week-old mice of test group 16 which were administered with test sample 6 for a period of 10 weeks, which were lower compared to the mean of the load (10.7±1.3 mN) obtained for test group 15 in which hardening of the lens with aging was observed. This result indicates that hardening of the lens with aging was inhibited in test group 16, which were administered with test sample 6 for a period of 10 weeks. Surprisingly, the mean of the load obtained for the lenses of test group 16 was lower even compared to the mean of the load (10.0±1.0 mN) obtained for the 9-week-old mice before administration of samples. This result indicates that not only hardening of the lens with aging was inhibited but also the lens was softened by administration of test sample 6 containing glycosyl hesperetin.

Meanwhile, as shown in Table 4, the mean of the load required for producing 15% dents of the lens, which is an indicator of the hardness of the lens, was 10.0±1.0 mN for 9-week-old mice before administration of the samples, but the mean of the load was increased up to 10.7±0.5 mN for 24-week-old mice of the group that ingested control sample (test group 17), indicating progress of hardening of the lens with aging. In contrast, the mean of the load was 7.6±1.3 mN for 24 -week-old mice of test group 18 which were administered with test sample 6 for a period of 15 weeks, which were remarkably lower compared to the mean of the load (10.7±0.5 mN) obtained for test group 17 in which hardening of the lens with aging was observed. This result indicates that hardening of the lens with aging was inhibited in test groups 18, which were administered with test sample 6 for a period of 15 weeks. Surprisingly, the mean of the load obtained for the lenses of test group 18 was remarkably lower even compared to the mean of the load (10.0±1.0 mN) obtained for the 9-week-old mice before administration of samples. This result indicates that not only hardening of the lens with aging was inhibited but also the lens was softened by continuous administration of test sample 6 containing glycosyl hesperetin.

In addition to the effect of decreasing hardening of the lens with aging by intake of the aqueous solution containing 1% by mass or 2% by mass of glycosyl hesperetin as confirmed in Experiment 3, the effect of decreasing hardening of the lens with aging by intake of the aqueous solution containing even as low as 0.1% by mass of glycosyl hesperetin was confirmed in Experiment 4. This result indicates that glycosyl hesperetin has the excellent effect of inhibiting hardening of the lens and is very useful as an active ingredient of the agent for adjusting hardness of a lens of an eye. Furthermore, it was confirmed that the continuous intake of the aqueous solution containing 0.1% by mass of glycosyl hesperetin not only inhibits the hardening of the lens but also decreases the hardness of the lens below that at the beginning of the experiment, as confirmed in Experiment 3 that the continuous intake of the aqueous solution containing 1% by mass or 2% by mass of glycosyl hesperetin not only inhibits the hardening of the lens but also decreases the hardness of the lens below that at the beginning of the experiment. This result indicates that glycosyl hesperetin has the effect of softening the lens and is useful as an active ingredient of the agent for adjusting hardness of a lens of an eye.

Experiment 5: Effect of Administration of Glycosyl Hesperetin at Low Dose on Hardness of the Lens In Experiments 3 and 4, the effect of inhibiting hardening of the lens and the effect of softening the lens by a long-term administration of glycosyl hesperetin were observed. In this experiment, the hardness of the lens after administration of a sample containing glycosyl hesperetin at a lower concentration than the samples of Experiments 3 and 4 or control sample for a shorter period than in Experiment 4 was measured.

Experiment 5-1: Preparation of Test Sample

The glycosyl hesperetin powder obtained in Experiment 1-1 was dissolved in tap water to a concentration of 0.15% by mass to obtain test sample 7. As a control sample, tap water was used.

Experiment 5-2: Dosing Study of Glycosyl Hesperetin at Low Dose

Male C57BL/6JJ mice of 9 weeks old were divided into the following three groups: Group before administration of samples, test group 19 (group administered with control sample) and test group 20 (group administered with test sample 7). Each group consisted of 3 mice. Test group 20 was given 0.2 mL of test sample 7 obtained in Experiment 5-1 (10 mL/kg-body weight, equivalent to a dose of 10 mg/kg-body weight in terms of a dose of glycosyl hesperetin) orally with a gastric tube once a day for 15 days among the test period of 19 days. Meanwhile, test group 19 was given tap water orally with a gastric tube once a day for 15 days among the test period of 19 days. The lenses were collected when the mice were 9 weeks old for the group before administration of samples and after 6 hours of the 15th administration with a gastric tube (when the mice were 11 weeks old) for test groups 19 and 20. The hardness of the lens was measured promptly after collection. The same breeding condition as described in Experiment 3 was used.

Evaluation Items and Evaluation Method

The hardness of the lens of 9-week-old mice before administration of samples and the hardness of the lens of 11-week-old mice after administration of each sample was evaluated. The measurement of the hardness of the lens was conducted in the same manner as described in Experiment 1. As an indicator of the lens hardness after intake of each sample against hardening of the lens during breeding period, the mean of the load required for producing 15% dents of the lens and its standard error were shown in Table 5.

Statistical Analysis

Measured values were expressed as mean±standard error (SE). Statistical analysis was performed using SPSS software version 24 (IBM Japan, Ltd., Tokyo, Japan) and Student's t-test was used to compare the group before administration of samples and each test group. A significance level (p value) of less than 0.05 (less than 5% risk) was judged to be significant.

TABLE 5

| | | Load (mN) | |
|---|---|---|---|
| | | 9-week-old (Before administration) | 11-week-old (Administration for 15times) |
| Test Group 19 | Control sample ingestion group | 11.4 ± 0.8 | 11.7 ± 0.7 |
| Test Group 20 | Test sample 7 ingestion group | | 9.0 ± 0.3* |

*$p < 0.05$ vs 9-week-old (before administration) group

As shown in Table 5, the mean of the load required for producing 15% dents of the lens, which is an indicator of the hardness of the lens, was 11.4±0.8 mN for 9-week-old mice before administration of samples, but the mean of the load was increased up to 11.7±0.7 mN for 11-week-old mice of the group that ingested control sample (test group 19), indicating hardening of the lens with aging. In contrast, the mean of the load was 9.0±0.3 mN for 11-week-old mice of the group administered with test sample 7 (test group 20), which were lower compared to the mean of the load (11.7±0.7 mN) obtained for the group administered with control sample (test group 19). This result indicates that hardening of the lens with aging was inhibited in test group 20, which ingested test sample 7. Surprisingly, the mean of the load obtained for the lenses of test group 20 was remarkably lower even compared to the mean of the load (11.4±0.8 mN) obtained for the 9-week-old mice before administration of samples. This result indicates that not only hardening of the lens with aging was inhibited but also the lens was softened by continuous administration of test sample 7.

In Experiment 5, it was confirmed that the hardening of the lens with aging is inhibited even by the continuous and short-term intake of the aqueous solution containing 0.15% by mass of glycosyl hesperetin. This result indicates that glycosyl hesperetin has the effect of inhibiting hardening of the lens and is useful as an active ingredient of the agent for adjusting hardness of a lens of an eye. Furthermore, it was confirmed that the continuous intake of the aqueous solution containing 0.15% by mass of glycosyl hesperetin not only inhibits the hardening of the lens with aging but also decreases the hardness of the lens below that at the beginning of the experiment. These results indicates that glycosyl hesperetin has the effect of softening the lens and is useful as an active ingredient of the agent for adjusting hardness of a lens of an eye.

Experiment 6: Effect of Long-Term Ingestion of Glycosyl Hesperetin on Near Visual Acuity In Experiments 1 to 5, the ingestion of glycosyl hesperetin was found to have the effect of inhibiting hardening of the lens and the effect of softening the lens. Therefore, we measured near visual acuity after long-term ingestion of glycosyl hesperetin in humans and investigated into the effect of ingestion of glycosyl hesperetin on near visual acuity of humans.

Experiment 6-1: Selection of Subjects

For 51 healthy adult males and females (31 to 61 years old) as candidates, the near point distance was measured in order to select subjects for a later described experiment. The near point distance is one of the indicators of presbyopia, and in this experiment, it was measured using a near point distance measuring apparatus that was prepared by the inventors. In detail, for 5 minutes before the measurement, the candidates were allowed to rest in a sitting position, under refractive correction (If the candidates wear glasses, they keep the glasses on.), and in an environment where they could not see their smartphones, PC displays, or the like. The near point distance was then measured by the following procedure. First, the candidate was made to touch the forehead to the forehead fixing plate on the near point distance measuring apparatus. From the state that the forehead fixing plate and a movable plate to which a newspaper article is attached were in contact, the candidate was made to move the movable plate gradually away from the candidate along the direction parallel to the floor. The candidate was made to stop the movable plate at the point (near point) where the characters of the newspaper article attached to the movable plate were in focus, and the distance from the forehead fixing plate to the movable plate was measured using a ruler. The near point distance was obtained by adding the distance measured and the thickness of the forehead fixing plate. The measurement of the near point distance was repeated three times for each candidate. A candidate with the average near point distance of 25 to 35 cm, which indicates early presbyopia, under refractive correction with a binocular distance vision of 0.7 or more in decimal visual acuity was selected as a subject and in total 32 candidates (40 to 61 years old) were selected as subjects. The 32 candidates were divided into two groups so that sex, age, and near visual acuity which is described later were even.

After the subjects were allowed to rest in a sitting position, under refractive correction, and in an environment where they could not see their smartphones, PC displays, or the like for 5 minutes, binocular near visual acuity was measured under refractive condition with a binocular distance vision of 0.7 or more in decimal visual acuity using a C&E near vision card with a 40 cm cord (#7280, T.M.I. Company, Limited, Saitama, Japan). In detail, the card with optotype symbols such as Landolt rings was placed at the same height as the eyes of the subject in the upright state and the subject was asked to answer the optotype symbol while maintaining the distance between the eyes and the card by keeping the 40 cm cord connected to the card from loosening. The measurement was continued using smaller optotype symbols until the subject hesitated or failed to identify the optotype symbols. The average value of the near visual acuity for the 32 subjects was 0.12 and ranged from −0.15 to 0.65. Here, logMAR visual acuity, which can be numerically processed, was used to express near visual acuity.

Experiment 6-2: Preparation of Test Sample

According to the conventional method, test sample 8 (Mass: 755 mg per tablet) in the form of a tablet having the composition shown in below Table 6, which contains glucosyl hesperidin (product name "Hayashibara Hesperidin 5", Hayashibara Co., Ltd., Okayama Japan) as glycosyl hesperetin, and control sample (Mass: 758 mg per tablet) having the similar appearance, flavor, and taste as test sample 8 were prepared.

TABLE 6

| | Formulation (% by mass) | |
|---|---|---|
| | Test Sample 8 | Control Sample |
| Maltose | 35.427 | 35.287 |
| Erythritol | 16.000 | 15.937 |
| Yuzu juice powder | 10.000 | 9.960 |
| Glycosyl hesperetin | 35.000 | — |
| Dextrin | — | 34.727 |
| Sucrose fatty acid ester | 1.200 | 1.591 |
| Flavoring agent | 1.000 | 0.996 |
| Acidulant | 1.000 | 0.996 |
| Aspartame | 0.200 | 0.199 |
| Sucralose | 0.058 | 0.058 |
| Acesulfame potassium | 0.035 | 0.035 |
| Adhesives (pullulan) | 0.080 | 0.080 |
| Safflower pigment | — | 0.135 |

Figure 13:
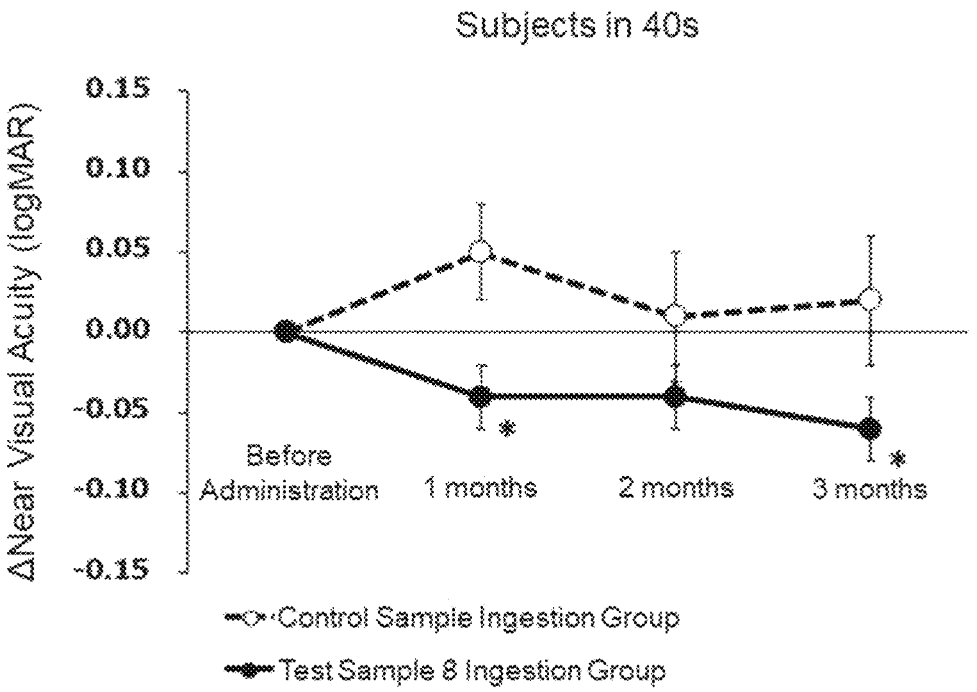
FIG. 13 The figure showing the changes in near visual acuity of human subjects (at the age of 40s), when taking a test sample containing glycosyl hesperetin or a control sample for 3 months.
Figure 14:
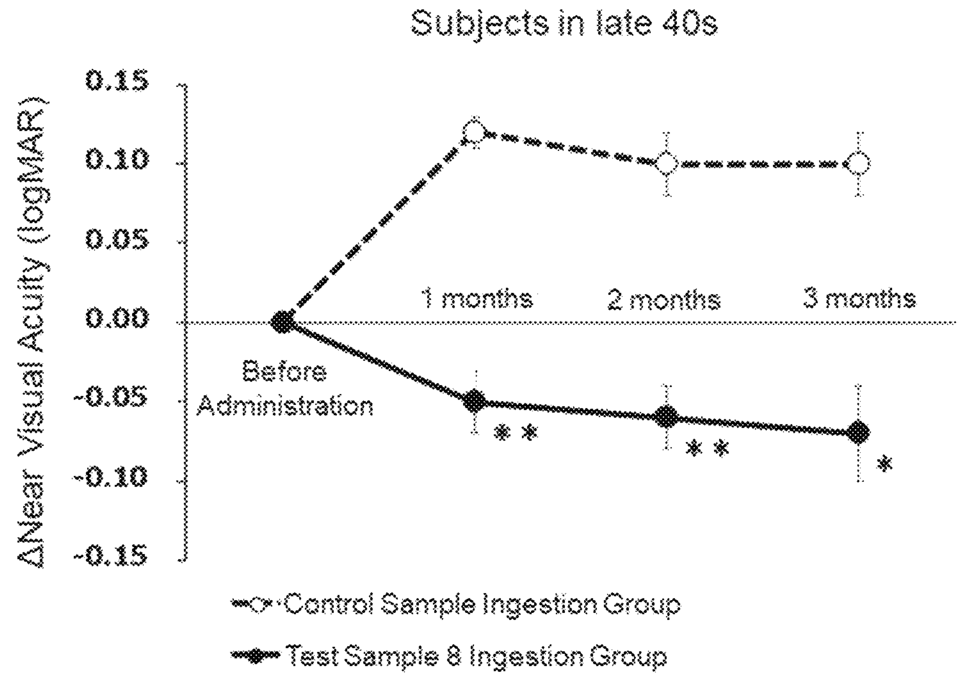
FIG. 14 The figure showing the changes in near visual acuity of human subjects (at the age of late 40s), when taking a test sample containing glycosyl hesperetin or a control sample for 3 months.

Experiment 6-3: Effect of Long-Term Ingestion of Glycosyl Hesperetin on Near Visual Acuity Without letting the subjects know whether the sample to be ingested was test sample 8 or control sample, they were made to ingest two tablets of test sample 8 or control sample once a day at any time for 3 consecutive months. Near visual acuity was measured using the same method as in Experiment 6-1 above, and the measurement was performed before the start of ingestion and 1, 2, and 3 months after the start of ingestion. The study design was a randomized double-blind placebo-controlled study. Change in near visual acuity compared to before the start of ingestion was analyzed for subjects in their 40s and late 40s, where the decrease in near visual acuity with aging is generally most remarkably observed. The obtained results were shown in Table 7 and FIG. 13 and FIG. 14.

<Statistical Analysis>

Measured values were expressed as mean±standard error (SE). Statistical analysis was performed using SPSS Statistics 26 (IBM Japan, Ltd., Tokyo, Japan) and Mann-Whitney U test was performed at each measurement point. A significance level (p value) of less than 0.05 (less than 5% risk) was judged to be significant.

TABLE 7

| | | Change in Near Visual Acuity (logMAR) | | |
|---|---|---|---|---|
| | | 1 month from start of ingestion | 2 months from start of ingestion | 3 months from start of ingestion |
| Subjects in 40s | Control sample ingestion group | 0.05 ± 0.03 | 0.01 ± 0.04 | 0.02 ± 0.04 |
| | Test sample ingestion group | −0.04 ± 0.02* | −0.04 ± 0.02 | −0.06 ± 0.02* |
| Subjects in late 40s | Control sample ingestion group | 0.12 ± 0.01 | 0.10 ± 0.02 | 0.10 ± 0.02 |
| | Test sample ingestion group | −0.05 ± 0.02** | −0.06 ± 0.02** | −0.07 ± 0.03* |

*$p < 0.05$ vs Control Sample Ingestion Group
**$p < 0.01$ vs Control Sample Ingestion Group As shown in Table 7, among subjects in their 40s (40-49 years old, n=17), the average values of the changes in near visual acuity in subjects who ingested control sample (43-49 years old, n=9) were 0.05±0.03, 0.01±0.04, and 0.02±0.04 after one month, two months, and three months from the start of sample ingestion, respectively, wherein the gradual decrease in near visual acuity was observed. In contrast, the average values of the changes in near visual acuity in subjects who ingested test sample 8 (40-49 years, n=8) were −0.04±0.02, −0.04±0.02, and −0.06±0.02 after one month, two months, and three months from the start of sample ingestion, respectively, wherein rather the gradual improvement in near visual acuity was observed. In particular, after one month and three months from the start of sample ingestion, the remarkable decrease in changes in near visual acuity was observed in subjects who ingested test sample 8, compared to subjects who ingested control sample. This result indicates that decline of near visual acuity was remarkably inhibited in subjects in their 40s who ingested test sample 8, and surprisingly further that not only decline of near visual acuity was inhibited but also near visual acuity was improved. Furthermore, among subjects in their late 40s (46-49 years old, n=10), the average values of the changes in near visual acuity in subjects who ingested control sample (46-49 years old, n=5) were 0.12±0.01, 0.10±0.02, and 0.10±0.02 after one month, two months, and three months from the start of sample ingestion, respectively, wherein the more pronounced decrease in near visual acuity than for subjects in 40s was observed. In contrast, the average values of the changes in near visual acuity in subjects who ingested test sample 8 (46-49 years, n=5) were −0.05±0.02, −0.06±0.02, and −0.07±0.03 after one month, two months, and three months from the start of sample ingestion, respectively, wherein the more pronounced decrease in changes in near visual acuity, that is, improvement in near visual acuity was observed. This result indicates that decline of near visual acuity was inhibited in subjects in their late 40s who ingested test sample 8, and further that near visual acuity was markedly improved. The above results indicate that the long-term oral ingestion of glycosyl hesperetin inhibits decline of near visual acuity with aging and improves near visual acuity. This result indicates that glycosyl hesperetin has the effect of preventing or improving decline of near visual acuity or poor focus with aging and is very useful as an active ingredient of the agent for adjusting hardness of a lens of an eye.

Hereinafter, the present invention is described in further detail based on examples, but the present invention is not limited to these specific examples.

Example 1

Agent for Adjusting Hardness of a Lens of an Eye in the Form of a Powder

A commercially available α-glucosyl hesperidin-containing powder (product name "Hayashibara Hesperidin S", Hayashibara Co., Ltd., Okayama Japan) was used as an agent for adjusting hardness of a lens of an eye. This product exhibiting the effect of softening the lens or the effect of inhibiting hardening of the lens is an agent for adjusting hardness of a lens of an eye with excellent storage stability and heat stability, which can be taken orally on a daily basis by adding to various beverages such as water, tea, black tea, coffee, etc., and other foods and beverages.

Example 2

Agent for Adjusting Hardness of a Lens of an Eye in the Form of a Tablet

One (1) part by mass of glycosyl hesperetin-containing powder (α-glucosyl hesperidin 82% by mass, hesperidin 1% by mass, 7-O-β-glucosyl hesperetin 8% by mass, and other components 9% by mass) (prepared by Hayashibara Co., Ltd.), 19 parts by mass of α,α-trehalose dihydrate crystal-containing powder (product name "TREHA", Hayashibara Co., Ltd., Okayama, Japan), 0.1 part by mass of lutein, 0.1 parts by mass of astaxanthin were uniformly mixed and tableted according to the conventional method to obtain an agent for adjusting hardness of a lens of an eye in the form of a tablet with a weight of 250 mg per tablet. This product exhibits the excellent effect of softening the lens or inhibiting hardening of the lens. By allowing patients who suffer from presbyopia, people who are concerned with poor focus or decline of near visual acuity with aging, or people who are at risk of developing presbyopia to take this product usually in an amount of 10 to 5000 mg of the glycosyl hesperetin in terms of hesperidin equivalent per adult per day on a daily basis, the symptoms of presbyopia or poor focus with aging may be alleviated or improved, and the onset of presbyopia may be effectively delayed or prevented.

Example 3

Agent for Adjusting Hardness of a Lens of an Eye in the form of a Soft Drink In 5,000 parts by mass of water, 200 parts by mass of sugar, 100 parts by mass of α,α-trehalose dihydrate crystal-containing powder (product name "TREHA", Hayashibara Co., Ltd., Okayama, Japan), 6 parts by mass of citric acid, 6 parts by mass of sodium chloride, 0.2 parts by mass of potassium chloride, 0.05 parts by mass of calcium lactate, 0.01 parts by mass of magnesium chloride, 5 parts by mass of α-glucosyl hesperidin crystal-containing powder (Purity: 99% by mass or more, prepared by Hayashibara Co., Ltd., Okayama, Japan) and 0.1 parts by mass of ascorbic acid 2-glucoside anhydrous crystal-containing powder (product name "Ascofresh", Hayashibara Co., Ltd., Okayama, Japan) were uniformly dissolved to obtain an agent for adjusting hardness of a lens of an eye in the form of a soft drink. This product exhibits the effect of softening the lens or the effect of inhibiting hardening of the lens, and is useful as an agent for adjusting hardness of a lens of an eye with good flavor and taste for improving, alleviating, and/or preventing poor focus or decline of near visual acuity, such as presbyopia, caused by aging and various diseases.

Example 4

Agent for Adjusting Hardness of a Lens of an Eye in the Form of a Hard Candy

The mixture of 10 parts by mass of α,α-trehalose dihydrate crystal-containing powder (product name "TREHA", Hayashibara Co., Ltd., Okayama, Japan) and 20 parts by mass of water was concentrated under reduced pressure at 155° C. until the water content was reduced to about 2% or less. Then, the concentrate was cooled to 120° C., to which 0.5% by mass of ascorbic acid 2-glucoside anhydrous crystal-containing powder (product name "Ascofresh", Hayashibara Co., Ltd., Okayama, Japan), 0.5 parts by mass of α-glucosyl hesperidin-containing powder (product name "Hayashibara Hesperidin S", Hayashibara Co., Ltd., Okayama, Japan), 0.01 parts by mass of lutein, 0.01 parts by mass of anthocyanin, and an appropriate amount of lemon flavor were mixed. The obtained mixture was then formed and packaged in accordance with the conventional method to obtain an agent for adjusting hardness of a lens of an eye in the form of a hard candy. This product exhibits the effect of softening the lens or the effect of inhibiting hardening of the lens, and is useful as an agent for adjusting hardness of a lens of an eye with good flavor and taste for improving, alleviating, and/or preventing poor focus or decline of near visual acuity, such as presbyopia, caused by aging and various diseases.

Example 5

Agent for Adjusting Hardness of a Lens of an Eye in the Form of a Chewing Gum

Three (3) parts by mass of a gum base was heated and melted until soft, to which 6 parts by mass of α,α-trehalose (product name "TREHA", Hayashibara Co., Ltd., Okayama Japan) and 1 part by mass of glycosyl hesperetin-containing powder (α-glucosyl hesperidin 82% by mass, hesperidin 1% by mass, 7-O-β-glucosyl hesperetin 8% by mass, and other components 9% by mass) (prepared by Hayashibara Co., Ltd.) were added and further 0.1 parts by mass of berry extract and an appropriate amount of a coloring agent and a flavoring agent were mixed respectively. The obtained mixture was then kneaded, molded, and packaged, in accordance with a conventional method, to obtain a chewing gum containing α-glucosyl hesperidin. This product exhibits the effect of softening the lens or the effect of inhibiting hardening of the lens, and is useful as an agent for adjusting hardness of a lens of an eye with good flavor and texture for improving, alleviating, and/or preventing poor focus or decline of near visual acuity, such as presbyopia, caused by aging and various diseases.

Example 6

Agent for Adjusting Hardness of a Lens of an Eye in the Form of an Oral Tube Feeding Nutrition Thirty (30) parts by mass of maltose (product name "Maltose PH", Hayashibara Co., Ltd., Okayama, Japan), 3 parts by mass of monosodium glutamate, 2 parts by mass of glycine, 2 parts by mass of sodium chloride, 0.3 parts by mass of magnesium carbonate, 1 part by mass of calcium lactate, 5 parts by mass of α-glucosyl hesperidin crystal-containing powder (purity: 99% by mass or higher; prepared by Hayashibara Co., Ltd., Okayama Japan), 0.02 parts by mass of vitamin A, 0.02 parts by mass of vitamin B2, 0.02 parts by mass of vitamin B6 and 0.02 parts by mass of vitamin B12 were mixed. The obtained mixture was divided into 30 g portions in laminated aluminum bags and heat-sealed to obtain an agent for adjusting hardness of a lens of an eye in the form of an oral tube feeding nutrition. This product, exhibiting the effect of softening the lens or the effect of inhibiting hardening of the lens, may be dissolved in about 250 to 500 mL of sterile water per bag and advantageously used as an agent in a liquid form, which can be taken orally or through a feeding tube as an agent for adjusting hardness of a lens of an eye for improving, alleviating, and/or preventing poor focus or decline of near visual acuity, such as presbyopia, caused by aging and various diseases.

Example 7

Agent for Adjusting Hardness of a Lens of an Eye in the Form of a Capsule

Ten (10) parts by mass of calcium acetate monohydrate, 50 parts by mass of magnesium L-lactate trihydrate, 57 parts by mass of maltose, 20 parts by mass of α-glucosyl hesperidin-containing powder (product name "Hayashibara hesperidin S", Hayashibara Co., Ltd., Okayama, Japan), 12 parts by mass of γ-cyclodextrin inclusion complex containing 20% vitamin E, and 1 part by mass of blueberry extract powder were uniformly mixed, and granulated by a granulating machine. The obtained granules were encapsulated in a gelatin capsule according to the conventional method to obtain an agent for adjusting hardness of a lens of an eye in the form of a capsule, which contained 150 mg of content per capsule. This product exhibits the effect of softening the lens or the effect of inhibiting hardening of the lens, is useful as an agent for improving, alleviating, and/or preventing poor focus or decline of near visual acuity, such as presbyopia, caused by aging and various diseases.

Example 8

Agent for Adjusting Hardness of a Lens of an Eye in the Form of a Capsule

Ten (10) parts by mass of calcium acetate monohydrate, 50 parts by mass of magnesium L-lactate trihydrate, 57 parts by mass of maltose, 20 parts by mass of α-glycosyl hesperetin-containing powder (α-glucosyl hesperidin 82% by mass, hesperidin 1% by mass, 7-O-β-glucosyl hesperetin 8% by mass, and other ingredients 9% by mass) (prepared by Hayashibara Co., Ltd., Okayama, Japan), 10 parts by mass of γ-cyclodextrin inclusion complex containing 20% vitamin A, 0.5 parts by mass of γ-cyclodextrin inclusion complex containing 20% DHA, 0.5 parts by mass of γ-cyclodextrin inclusion complex containing 20% EPA, 0.5 parts by mass of γ-cyclodextrin inclusion complex containing 20% 6-carotene, and 0.5 parts by mass of γ-cyclodextrin inclusion complex containing 20% α-lipoic acid were uniformly mixed, and granulated by a granulating machine. The obtained granules were encapsulated in a gelatin capsule according to the conventional method to obtain an agent for adjusting hardness of a lens of an eye in the form of a capsule, which contained 150 mg of content per capsule. This product exhibits the effect of softening the lens or the effect of inhibiting hardening of the lens, and is useful as an agent for improving, alleviating, and/or preventing poor focus or decline of near visual acuity, such as presbyopia, caused by aging and various diseases.

Example 9

Agent for Adjusting Hardness of a Lens of an Eye in the Form of a Soft Capsule Ten (10) parts by mass of α-glucosyl hesperidin crystal-containing powder (purity: 99% by mass or higher; prepared by Hayashibara Co., Ltd., Okayama Japan), 10 parts by mass of blueberry fruit extract, 2 parts by mass of cassis extract, 1 part by mass of delphinidin glucoside, 2 parts by mass of 6-carotene 30% suspension, 0.1 parts by mass of vitamin A1, 0.1 parts by mass of vitamin E, 0.1 parts by mass of astaxanthin, 0.1 parts by mass of lutein, 5 parts by mass of glycerin fatty acid ester, 20 parts by mass of soybean lecithin, and 65 parts by mass of safflower oil were uniformly mixed, and the mixture was coasted with soft capsule film containing gelatin and glycerin according to the conventional method to obtain an agent for adjusting hardness of a lens of an eye in the form of s soft capsule, which contained 350 mg of content per capsule. This product exhibits the effect of softening the lens or the effect of inhibiting hardening of the lens and is useful as an agent for improving, alleviating, and/or preventing poor focus or decline of near visual acuity, such as presbyopia, caused by aging and various diseases.

Example 10

Agent for Adjusting Hardness of a Lens of an Eye in the Form of a Tablet

Twenty nine (29) parts by mass of α-glucosyl hesperidin-containing powder (product name "Hayashibara hesperidin 5", Hayashibara Co., Ltd., Okayama, Japan), 70 parts by mass of maltose (product name "Sunmalt", Hayashibara Co., Ltd., Okayama, Japan), 1 part by mass of sucrose stearate, 0.1 parts by mass of astaxanthin, 0.1 parts by mass of green tea extract, 0.1 part by mass of *Ginkgo biloba* leaf extract, 0.1 part by mass of grape seed extract were uniformly mixed and tableted according to the conventional method to obtain an agent for adjusting hardness of a lens of an eye in the form of a tablet. Since this product is excellent in the effect of adjusting the lens hardness, it has effect of improving, alleviating, and/or preventing poor focus or decline of near visual acuity, such as presbyopia, caused by aging and various diseases, and is useful also as a healthy food.

Example 11

Agent for Adjusting Hardness of a Lens of an Eye in the Form of a Powder

Ten (10) parts by mass of glycosyl hesperetin-containing powder (82% by mass of α-glucosyl hesperidin, 1% by mass of hesperidin, 8% by mass of 7-O-β-glucosyl hesperetin, and 9% by mass of other ingredients) (prepared by Hayashibara Co., Ltd., Okayama, Japan), 3 parts by mass of sucrose, 1 part by mass of maltitol, and 15 parts by mass of water-soluble dietary fiber (product name "Fibryxa", Hayashibara Co., Ltd., Okayama, Japan) were mixed by stirring and then divided into 5 g portions in light and moisture-resistant packaging containers in stick form, to obtain an agent for adjusting hardness of a lens of an eye in the form of a powder. This product exhibits the effect of softening the lens or the effect of inhibiting hardening of the lens, and may be taken orally on a daily basis in an amount of 1 to 3 sachets of the product per day by adding to various beverages such as water, tea, black tea, coffee, etc., and other foods and beverages. Since this product is excellent in the effect of adjusting the lens hardness, it has the effect of improving, alleviating, and/or preventing poor focus or decline of near visual acuity, such as presbyopia, caused by aging and various diseases, and is useful also as a healthy food.

Example 12

Agent for Adjusting Hardness of a Lens of an Eye in the Form of a Tablet

Ten (10) parts by mass of L-ascorbic acid, 19 parts by mass of α-glucosyl hesperidin-containing powder (purity 99% by mass or more, prepared by Hayashibara Co., Ltd. Okayama, Japan), 70 parts by mass of maltose (product name "Sunmalt", Hayashibara Co., Ltd., Okayama, Japan), 1 part by mass of sucrose stearate, 0.01 parts by mass of zinc, 0.01 parts by mass of selenium, and 0.01 parts by mass of L-glutathione were uniformly mixed and tableted according to the conventional method to obtain an agent for adjusting hardness of a lens of an eye in the form of a tablet. This product exhibits the effect of softening the lens or the effect of inhibiting hardening of the lens and is useful as an agent for adjusting hardness of a lens of an eye with good flavor and texture. Since this product is excellent in the effect of adjusting the lens hardness, it has effect of improving, alleviating, and/or preventing poor focus or decline of near visual acuity, such as presbyopia, caused by aging and various diseases, and is useful also as a healthy food.

Example 13

Agent for Adjusting Hardness of a Lens of an Eye in the Form of a Gummy Candy One hundred and fifty (150) parts by mass of a commercially available α-maltosyl trehalose-containing syrup (product name "Hallodex", Hayashibara Co., Ltd., Okayama, Japan) was heated under reduced pressure and concentrated to reach a water content of 15% by mass. To the concentrate, 13 parts by mass of gelatin dissolved in 18 parts by mass of water according to the conventional method, 2 parts by mass of α-glucosyl hesperidin-containing powder (product name "Hayashibara Hesperidin 5", Hayashibara Co., Ltd., Okayama, Japan), 2 parts by mass of citric acid, 0.1 parts by pass of ascorbic acid 2-glucoside anhydrous crystal-containing powder (product name "Ascofresh", Hayashibara Co., Ltd., Okayama Japan), 0.1 parts by mass of glucosyl rutin, 0.1 parts by mass of sodium chloride, and an appropriate amount of coloring agents and flavoring agents were uniformly mixed, formed and packaged according to the conventional method to obtain an agent for adjusting hardness of a lens of an eye in the form of a gummy candy. This product exhibits the effect of softening the lens or the effect of inhibiting hardening of the lens and is useful as an agent for adjusting hardness of a lens of an eye with good flavor and texture. Since this product is excellent in the effect of adjusting the lens hardness, it has the effect of improving, alleviating, and/or preventing poor focus or decline of near visual acuity, such as presbyopia, caused by aging and various diseases, and is useful also as a healthy food.

Example 14

Agent for Adjusting Hardness of a Lens of an Eye in the Form of a Supplement One (1) part by mass of glycosyl hesperetin-containing powder (82% by mass of α-glucosyl hesperidin, 1% by mass of hesperidin, 8% by mass of 7-O-β-glucosyl hesperetin, 9% by mass of other ingredients) (prepared by Hayashibara Co., Ltd., Okayama, Japan), 50 parts by mass of water-soluble dietary fiber (product name "Fibryxa", sold by Hayashibara Co., Ltd., Okayama, Japan), 10 parts by mass of α,α-trehalose dihydrate crystal-containing powder (product name "TREHA", Hayashibara Co., Ltd., Okayama, Japan), 0.1 parts by mass of lycopene, 0.1 parts by mass of sesamin, 0.1 parts by mass of zeaxanthin, and 0.1 parts by mass of taurine were uniformly mixed and then divided into 3 g portions in a stick-shaped paper container whose inner surface is coated with an aluminum foil to obtain an agent for adjusting hardness of a lens of an eye in the form of a supplement. This product exhibits the effect of softening the lens or the effect of inhibiting hardening of the lens and is useful as an agent for adjusting hardness of a lens of an eye with good flavor and tastes. Since this product is excellent in the effect of adjusting the lens hardness, it has the effect of improving, alleviating, and/or preventing poor focus or decline of near visual acuity, such as presbyopia, caused by aging and various diseases, and is useful also as a healthy food.

Example 15

Agent for Adjusting Hardness of a Lens of an Eye in the Form of Yogurt

Forty (40) parts by mass of α-glucosyl hesperidin crystal-containing powder (purity: 99% by mass or higher; prepared by Hayashibara Co., Ltd., Okayama Japan), 800 parts by mass of a skimmed milk powder, and 4000 parts by mass of purified water were mixed and the raw material for fermented milk (yogurt mixt) was prepared. The obtained yogurt mix was heat sterilized at 95° C. for 10 minutes, and then cooled to 45° C. Next, 100 g of a mixed starter was inoculated to the yogurt mix and the obtained mixture was fermented in a tank at 47° C. for 5 hours, and then cooled to below 8° C. to obtain an agent for adjusting hardness of a lens of an eye in the form of a yogurt. This product exhibits the effect of softening the lens or the effect of inhibiting hardening of the lens and is useful as an agent for adjusting hardness of a lens of an eye with good flavor and tastes. By allowing patients who suffer from presbyopia, people who are concerned with poor focus with aging, or people who are at risk of developing presbyopia to take usually 100 to 500 g of the product per adult per day on a daily basis, the symptoms of presbyopia or poor focus with aging may be alleviated or improved, and the onset of presbyopia may be effectively delayed or prevented. Since this product is excellent in the effect of adjusting hardness of the lens, it has the effect of improving, alleviating, and/or preventing poor focus or decline of near visual acuity, such as presbyopia, caused by aging and various diseases, and is useful also as a healthy food.

Example 16

Agent for Adjusting Hardness of a Lens of an Eye in the Form of a Powder

Ten (10) parts by mass of α-glucosyl hesperidin-containing powder (product name "Hayashibara hesperidin 5", Hayashibara Co., Ltd., Okayama, Japan), 9 parts by mass of α,α-trehalose dihydrate crystal-containing powder (product name "TREHA", Hayashibara Co., Ltd., Okayama, Japan), 1 part by mass of lactosucrose (product name "Nyukaoligo", Hayashibara Co., Ltd., Okayama, Japan), 30 parts by mass of dextrin, 0.1 parts by mass of ascorbic acid 2-glucoside anhydrous crystal-containing powder (product name "Ascofresh", Hayashibara Co., Ltd., Okayama, Japan), 0.1 parts by mass of lutein, and 0.1 parts by mass of coenzyme Q10 were mixed by stirring, and then divided into 5 g portions in light and moisture-resistant packaging containers in stick form, to obtain an agent for adjusting hardness of a lens of an eye in the form of a powder. This product exhibits the effect of softening the lens or the effect of inhibiting hardening of the lens, has the effect of improving, alleviating, and/or preventing poor focus or decline of near visual acuity, such as presbyopia, caused by aging and various diseases, and may be taken orally on a daily basis in an amount of 1 to 2 sachets of the product per day by adding to various beverages such as water, tea, black tea, coffee, etc., and other foods and beverages.

Example 17

Agent for Adjusting Hardness of a Lens of an Eye in the Form of a Mixed Sweetener One hundred (100) parts by mass of isomerized liquid sugar, 1 part by mass of α,α-trehalose dihydrate crystal-containing powder (product name "TREHA", Hayashibara Co., Ltd., Okayama, Japan), 1 part by mass of lactosucrose (product name "NyukaOligo", Hayashibara Co., Ltd., Okayama, Japan), 2 parts by mass of glycosyl hesperetin-containing powder (82% by mass of α-glucosyl hesperidin, 1% by mass of hesperidin, 8% by mass of 7-O-β-glucosyl hesperetin, 9% by mass of other ingredients) (prepared by Hayashibara Co., Ltd., Okayama, Japan) were treated under heat at 80° C. for 30 minutes to obtain an agent for adjusting hardness of a lens of an eye in the form of a mixed sweetener. This product has good flavor and tastes and can be easily used for cooking various foods and beverages. This product is therefore useful as a liquid-type mixed sweetener with the excellent effect of adjusting the lens's hardness and the effect of improving, alleviating, and/or preventing poor focus or decline of near visual acuity, such as presbyopia, caused by aging and various diseases.

Example 18

Agent for Adjusting Hardness of a Lens of an Eye in the Form of a Health Supplemental Beverage Forty (40) parts by mass of isomerized sugar, 2 parts by mass of maltitol, 10 parts by mass of black vinegar, 5 parts by mass of apple vinegar, 2 parts by mass of citric acid, 2 parts by mass of malic acid, 2 parts by mass of concentrated apple juice, 3 parts by mass of α-glucosyl hesperidin crystal-containing powder (purity 99% by mass or more, Hayashibara Co., Ltd., Okayama, Japan) were mixed and dissolved to obtain an agent for adjusting hardness of a lens of an eye in the form of a health supplemental beverage. This product has good flavor and taste and is useful as an agent for adjusting hardness of a lens of an eye with the effect of improving, alleviating, and/or preventing poor focus or decline of near visual acuity, such as presbyopia, caused by aging and various diseases.

INDUSTRIAL APPLICABILITY

As described above, one aspect of the present invention relates to an agent for adjusting hardness of a lens of an eye, comprising a glycosyl hesperetin as an active ingredient, which is based on the unique finding that glycosyl hesperetin exerts the remarkable effect of inhibiting hardening of the lens. Furthermore, another aspect of the present invention relates to an agent for adjusting hardness of a lens of an eye, comprising a glycosyl hesperetin as an active ingredient, which is based on the unique finding that glycosyl hesperetin exerts the remarkable effect of softening the lens. The agent for adjusting hardness of a lens of an eye of the present invention is expected to exert effects of maintaining and recovering hardness of the lens when used by healthy and sick persons regularly. In particular, the agent for adjusting hardness of a lens of an eye of the present invention may be used as an agent for inhibiting hardening of a lens of an eye or an agent for softening a lens of an eye, and expected to prevent, alleviate, and improve poor focus or decline of near visual acuity, such as presbyopia, caused by aging and various diseases, by being applied to a person who are concerned with hardening of the lens or at the risk of developing hardening of the lens.

DESCRIPTION OF SYMBOLS

In FIG. 1,
○: Test Group 9 (Control sample ingestion group)
▲: Test Group 10 (Test sample 4 ingestion group)
■: Test Group 11 (Test sample 5 ingestion group)
In FIG. 2,
○: Test Group 9 (Control sample ingestion group)
▲: Test Group 10 (Test sample 4 ingestion group)
■: Test Group 11 (Test sample 5 ingestion group)
In FIG. 3,
○: Test Group 9 (Control sample ingestion group)
▲: Test Group 10 (Test sample 4 ingestion group)
■: Test Group 11 (Test sample 5 ingestion group)
In FIG. 4,
○: Test Group 12 (Control sample ingestion group)
▲: Test Group 13 (Test sample 4 ingestion group)
■: Test Group 14 (Test sample 5 ingestion group)
In FIG. 5,
○: Test Group 12 (Control sample ingestion group)
▲: Test Group 13 (Test sample 4 ingestion group)
■: Test Group 14 (Test sample 5 ingestion group)
In FIG. 6,
○: Test Group 12 (Control sample ingestion group)
▲: Test Group 13 (Test sample 4 ingestion group)
■: Test Group 14 (Test sample 5 ingestion group)
In FIG. 7,
○: Test Group 15 (Control sample ingestion group)
■: Test Group 16 (Test sample 6 ingestion group)
In FIG. 8,
○: Test Group 15 (Control sample ingestion group)
■: Test Group 16 (Test sample 6 ingestion group)
In FIG. 9,
○: Test Group 15 (Control sample ingestion group)
■: Test Group 16 (Test sample 6 ingestion group)
In FIG. 10,
○: Test Group 17 (Control sample ingestion group)
■: Test Group 18 (Test sample 6 ingestion group)
In FIG. 11,
○: Test Group 17 (Control sample ingestion group)
■: Test Group 18 (Test sample 6 ingestion group)
In FIG. 12,
○: Test Group 17 (Control sample ingestion group)
■: Test Group 18 (Test sample 6 ingestion group)
In FIG. 13,
○: Control sample ingestion group
■: Test sample 8 ingestion group
In FIG. 14,
○: Control sample ingestion group
■: Test sample 8 ingestion group

The invention claimed is:

1. A method for adjusting hardness of a lens of an eye of a subject, comprising orally administering to the subject an effective amount of α-glucosyl hesperidin.

2. The method according to claim 1, wherein the hardness of the lens is adjusted by inhibiting hardening of the lens.

3. The method according to claim 1, wherein the hardness of the lens is adjusted by softening the lens.

4. The method according to claim 1, wherein said oral administration continues for 4 or more consecutive days.

5. The method according to claim 1, wherein the subject is a human adult.

6. The method according to claim 1, wherein the adjusting hardness of the lens comprises preventing, alleviating or improving hardening of the lens with aging.

7. The method of claim 1, wherein said α-glucosyl is orally administered in the form of a food or beverage, supplement, health food, health supplement, food with health claims, dietary supplement, food with nutrient function claims, food with functional claims, food for specified health uses, food for special dietary uses, quasi-drug, and pharmaceutical, comprising said α-glucosyl hesperidin.

8. A method for preventing, alleviating or improving poor focus and/or decline of near visual acuity in a subject, comprising orally administering an effective amount of α-glucosyl hesperidin.

9. The method of claim 8, wherein the subject does not have a cataract.

* * * * *